United States Patent
Madhavamenon et al.

(10) Patent No.: US 9,682,112 B2
(45) Date of Patent: Jun. 20, 2017

(54) ULTRASOUND-ASSISTED CONTINUOUS EXTRACTION FOR COMPLETE FRAGMENTATION OF COCOA BEANS INTO FRACTIONS

(71) Applicant: AKAY FLAVOURS & AROMATICS PVT. LTD, Kerala (IN)

(72) Inventors: Krishnakumar Illathu Madhavamenon, Kerala (IN); Balu Paulose Maliakel, Kerala (IN)

(73) Assignee: AKAY FLAVOURS & AROMATICS PVT. LTD, Kerala (IN)

( * ) Notice: Subject to any disclaimer, the term of this patent is extended or adjusted under 35 U.S.C. 154(b) by 157 days.

(21) Appl. No.: 14/451,455

(22) Filed: Aug. 5, 2014

(65) Prior Publication Data
US 2015/0196610 A1   Jul. 16, 2015

(30) Foreign Application Priority Data
Aug. 5, 2013 (IN) .......................... 3504/CHE/2013

(51) Int. Cl.
| | | |
|---|---|---|
| *A61K 36/185* | (2006.01) | |
| *A61K 31/353* | (2006.01) | |
| *C12P 21/06* | (2006.01) | |
| *A23L 3/30* | (2006.01) | |
| *C12P 17/06* | (2006.01) | |
| *C12P 19/14* | (2006.01) | |
| *C12P 19/20* | (2006.01) | |
| *A61K 8/97* | (2017.01) | |
| *A61Q 19/00* | (2006.01) | |
| *A61Q 19/08* | (2006.01) | |
| *A61K 8/02* | (2006.01) | |
| *A23G 1/00* | (2006.01) | |
| *A23G 1/48* | (2006.01) | |
| *A23P 10/30* | (2016.01) | |
| *A23L 27/28* | (2016.01) | |
| *A23L 33/105* | (2016.01) | |
| *A23L 33/21* | (2016.01) | |

(52) U.S. Cl.
CPC .......... *A61K 36/185* (2013.01); *A23G 1/0006* (2013.01); *A23G 1/48* (2013.01); *A23L 3/30* (2013.01); *A23L 27/28* (2016.08); *A23L 33/105* (2016.08); *A23L 33/21* (2016.08); *A23P 10/30* (2016.08); *A61K 8/0212* (2013.01); *A61K 8/97* (2013.01); *A61K 31/353* (2013.01); *A61Q 19/00* (2013.01); *A61Q 19/08* (2013.01); *C12P 17/06* (2013.01); *C12P 19/14* (2013.01); *C12P 19/20* (2013.01); *C12P 21/06* (2013.01); *A23V 2002/00* (2013.01); *A61K 2236/00* (2013.01); *A61K 2800/522* (2013.01)

(58) Field of Classification Search
CPC .......... A23L 3/30; A23L 1/3002; A23L 27/28; A23L 33/21; A23L 33/105; A61K 36/185; A61K 31/353; A61K 8/97; A61K 8/0212; A61K 2236/00; A61K 2800/522; C12P 21/06; C12P 17/06; C12P 19/14; C12P 19/20; A23V 2002/00; A61Q 19/00; A61Q 19/08; A23G 1/0006; A23G 1/04; A23G 1/08; A23P 10/30

See application file for complete search history.

(56) References Cited

U.S. PATENT DOCUMENTS

| | | |
|---|---|---|
| 1,073,441 A | 9/1913 | Riddle et al. |
| 1,855,026 A | 4/1932 | Livingston |
| 1,925,326 A | 9/1933 | Harvey et al. |
| 4,390,698 A | 6/1983 | Chiouini et al. |
| 4,407,834 A | 10/1983 | Chiouini et al. |
| 4,444,798 A | 4/1984 | Magnolato et al. |
| 4,755,391 A | 7/1988 | Bigalli et al. |
| 4,904,773 A | 2/1990 | Yu et al. |
| 5,139,799 A * | 8/1992 | Palson ............... A23L 3/30 426/238 |
| 5,554,645 A | 9/1996 | Rommczyk, Jr. et al. |
| 6,627,232 B1 | 9/2003 | Hammerston, Jr. et al. |
| 7,368,144 B2 | 5/2008 | Lecoupeau et al. |
| 2003/0170199 A1 | 9/2003 | Le Clere et al. |
| 2004/0096566 A1 | 5/2004 | Lecoupeau et al. |
| 2004/0103334 A1 | 5/2004 | Pappalardo et al. |
| 2005/0164956 A1 | 7/2005 | Schmitz et al. |
| 2007/0134400 A1 | 6/2007 | Kealey et al. |
| 2008/0021227 A1 | 1/2008 | Romanczyk et al. |
| 2008/0051587 A1 | 2/2008 | Hammerstone et al. |
| 2008/0193629 A1 | 8/2008 | Pons-Andreu et al. |

(Continued)

FOREIGN PATENT DOCUMENTS

WO   2010/066015 A2   6/2010

OTHER PUBLICATIONS

A Comparative Study of the Seed Polyphenols of the Genus *Theobroma* by L. A. Griffiths Regional Research Centre, Imperial College of Tropical Agriculture, Trinidad (Received Jun. 8, 1959).
Enzyme Activities in Cocoa Beans During Fermentation Carl E Hansen,* Margarita del Olmo and Christine Burri Nestl*) Research Centre, Nestec Ltd, Vers-chez-les-Blanc, P O Box 44, CH-1000 Lausanne 26, Switzerland (Received Jan. 23, 1997; revised version received Jul. 22, 1997; accepted Oct. 22, 1997).
Polyphenols of Mature Plant, Seedling and Tissue Cultures of Theobroma Cacao Mahbubul A. F. Jalal and Hami~H A. C~Llin hpartrnent of Botany, University of Liverpool, Liverpool L69 3BX, U.K. (Revised received Apr. 1, 1977).

(Continued)

*Primary Examiner* — Anthony Weier
(74) *Attorney, Agent, or Firm* — Mark M. Friedman

(57) ABSTRACT

A process for the complete fractionation of cocoa beans with 'zero waste' into various value-added ingredients, a composition having cocoa polyphones/procyanidins and soluble dietary fiber, and a water dispersible and sustained release formulation of cocoa polyphones with cocoa soluble dietary fiber capable of forming a colloidal dispersion of bioactive cocoa polyphones in gastric fluid.

16 Claims, 13 Drawing Sheets

(56) References Cited

U.S. PATENT DOCUMENTS

2010/0062138 A1    3/2010  Cienfuegos-Jouellanos Fermandez et al.

OTHER PUBLICATIONS

Effects of Cocoa Extracts on Endothelium-Dependent Relaxation1 Malina Karim, Kellie McCormick and C. Tissa Kappagoda2 Department of Internal Medicine, University of California Davis, California 95616-8636, American Society for Nutrional Sciences (2000) pp. 2105s-2108s.
(−)-Epicatechin Content in Fermented and Unfermented Cocoa Beans H. Kim and P. G. Keeney. 1090-Journal of Food Science—vol. 49 (1984).
K Kondo, R Hifano, A Matsumoto, 0 Igarashr, H Itahura *Division of Clinical Nutrition, National Institute of Health and Nutrition and Insitute of Environmental Science for Human Life. Ochanomizu University, Tokyo 162. Japan vol. 348—Nov. 30, 1996, Inhibition of LDL Oxidation by Cocoa.
Cocoa Has More Phenolic Phytochemicals and a Higher Antioxidant Capacity than Teas and Red Wine Ki Won Lee, †, § Young Jun Kim,# Hyong Joo Lee,† and Chang Yong Lee*,§ Department of Food Science and Technology, School of Agricultural Biotechnology, Seoul National University, Seoul 151-742, South Korea; Department of Food Science and Technology, Journal of Agriculture Food Chemistry Published 2003 vol. 51 pp. 7292-7295.
Cocoa Procyanidins and Human Cytokine Transcription and Secretion1,2 Tin Mao,* Judy Van de Water,* Carl L. Keen,† Harold H. Schmitz** and M. Eric Gershwin*3 *Division of Rheumatology, Allergy and Clinical Immunology, and †Department of Nutrition, University of California at Davis, Davis, California 95616 and **Analytical and Applied Sciences, Mars, Incorporated, Hackettstown, New Jersey 07840, American Society for Nutritional Sciences Published 2000 pp. 2093s-2099s.
Cocoa and Wine Polyphenols Modulate Platelet Activation and Function1 Dietrich Rein,* Teresa G. Paglieroni,\ Debra A. Pearson,* Ted Wun,** Harold H. Schmitz,† Robert Gosselin†† and Carl L. Keen*2 *Department of Nutrition, University of California, Davis, Davis, CA 95616; †Sacramento Medical Foundation, Center for Blood Research, Sacramento, CA; **Division of Hematology and Oncology and ±Department of, Published 2000 pp. 2120s-2126s American Society for Nutritional Science.
Journal of Chromatography A, 654 (1993) 255-260 Elsevier Science Publishers B.V., Amsterdam CHROM. 25 502 Normal-phase high-performance separation of procyanidins from, Rigaud et al.
Chocolate procyanidins decrease the leukotriene-prostacyclin ratio in humans and human aortic endothelial cells 1-3 Derek D Schramm, Janice F Wang, Roberta R Holt, Jodi L Ensunsa, Jana L Gonsalves, Sheryl A Lazarus, Harold H Schmitz, J Bruce German, and Carl L Keen, American Journal of Clinical Nutrition (2001) vol. 73, pp. 36-40.
Colorimetry of Total Phenolics With Phosphomolybdic-Phosphotungstic Acid Reagents V. L. Singleton and Joseph A. Rossi, Jr.J, pp. 144-158.
Effects of cocoa powder and dark chocolate on LDL oxidative susceptibility and prostaglandin concentrations in humans1-3 Ying Wan, Joe A Vinson, Terry D Etherton, John Proch, Sheryl A Lazarus, and Penny M Kris-Etherton. The American Journal of Clinical Nutrition, 2001 vol. 74. pp. 596-602.
*Andrew L Waterhouse, Joseph R Shirley, Jennifer L Donovan Department of Viticulture and Enology, University of California, Davis, CA 95616, USA—vol. 348 • Sep. 21, 1996—The Lancet, Antioxidants in Chocolate.
Antioxidative effects of cocoa. [1983] Ziegleder G. Sandmeier D. Food and agricultural iorganization of the united nations. http://agris.fao.org/agrissearch/search.do?recordID=DE19850028150.
Eskes et al. Evidence for the Effect of the Cocoa Bean Flavour Environment during Fermentation of the Final Flavour Profile of Cocoa Liquor and Chocolate No date provided.

* cited by examiner

* indicates chiral center located at the $C_2$ and $C_3$-position of the (-)-Catechin (2S, 3R)

(-)-Epicatechin (2R, 3R)

Figure 2: Schematic representation of (A) ultrasound aided continuous extractor and (B) De-solventiser system developed for the direct extraction of cocoa beans
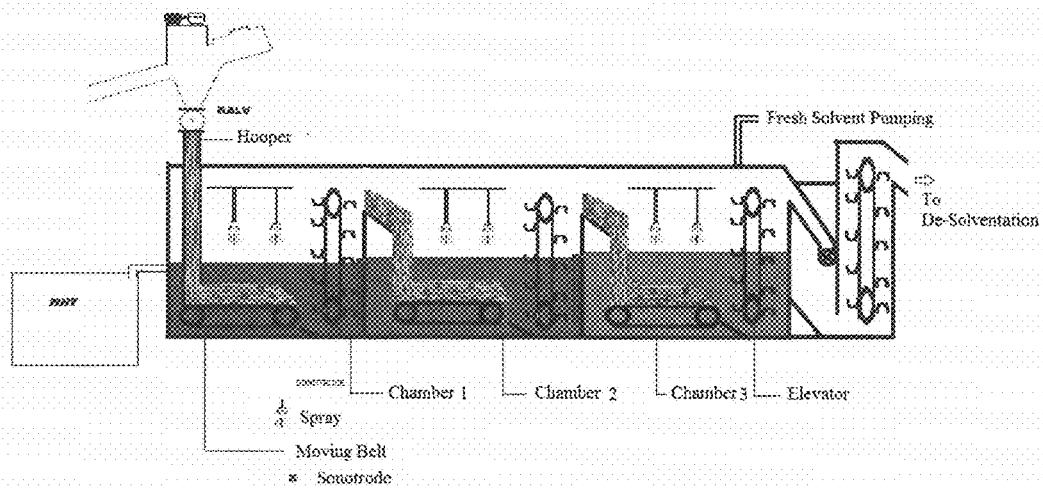
(B)
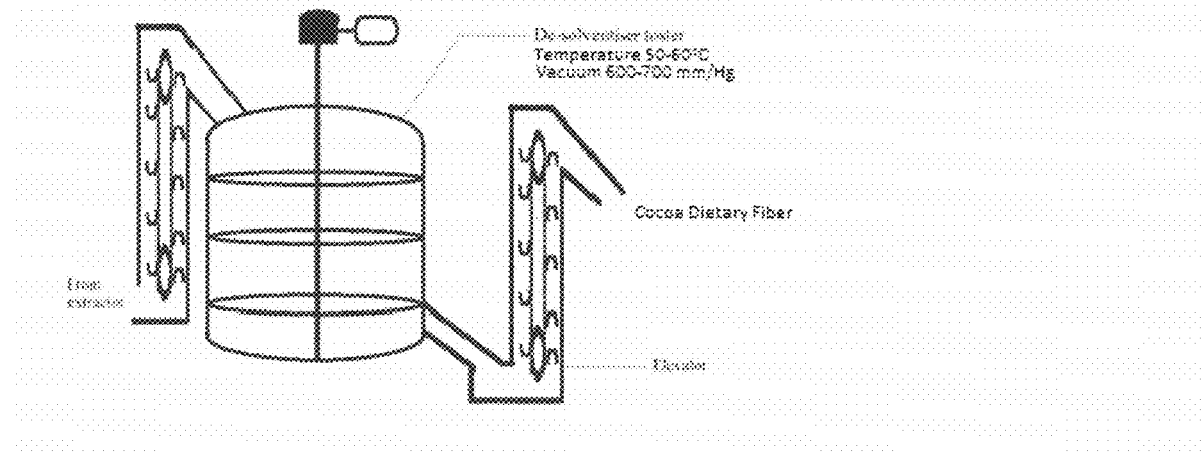

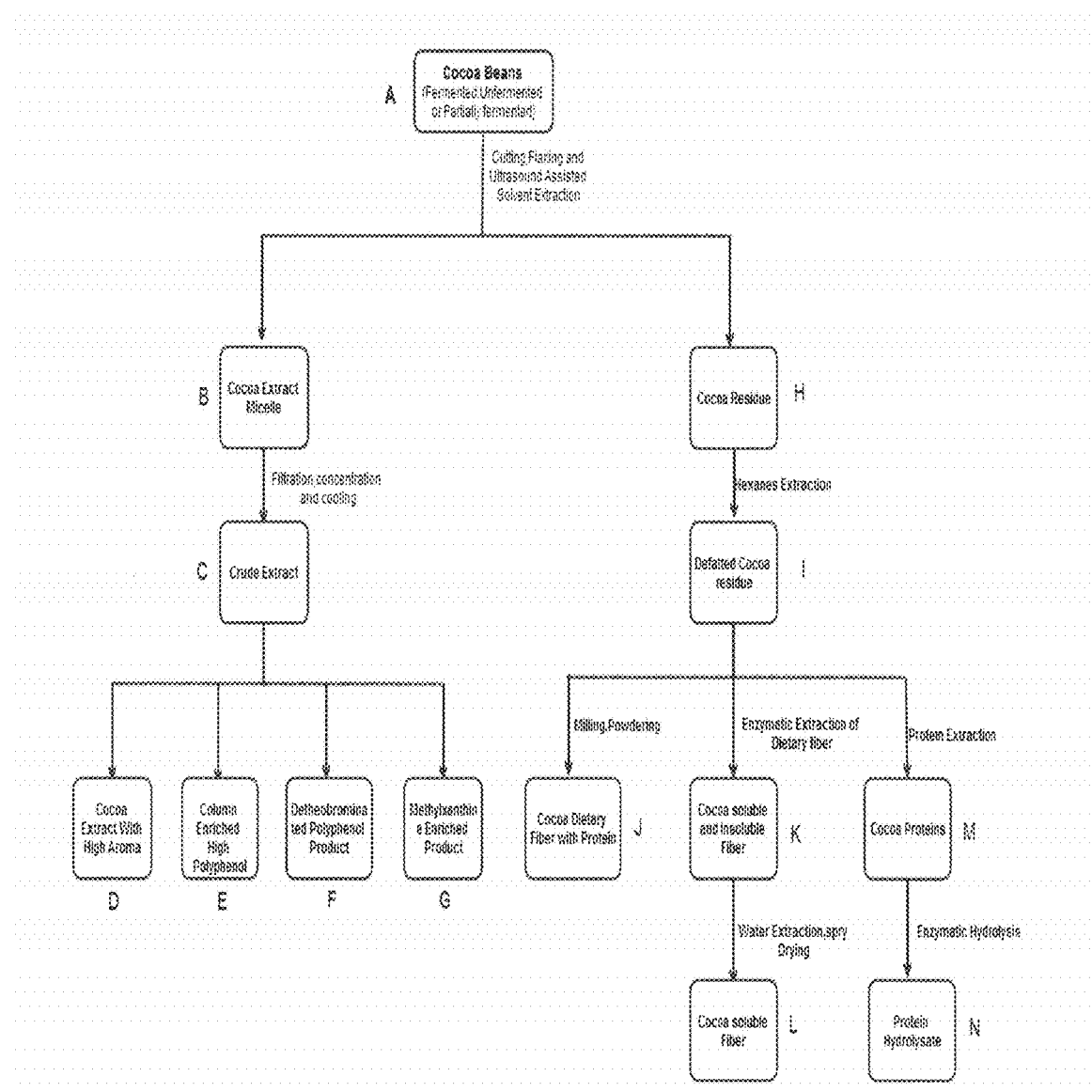
Figure 3: Schematic representation of various value-added products derived from cocoa beans with 'zero waste – green process'

Figure 4: HPLC-diode array profile at 280 nm (A) Cocoa extract with > 95% gallic acid equivalent polyphenol content containing theobromine and (B) its percentage composition.

(A)

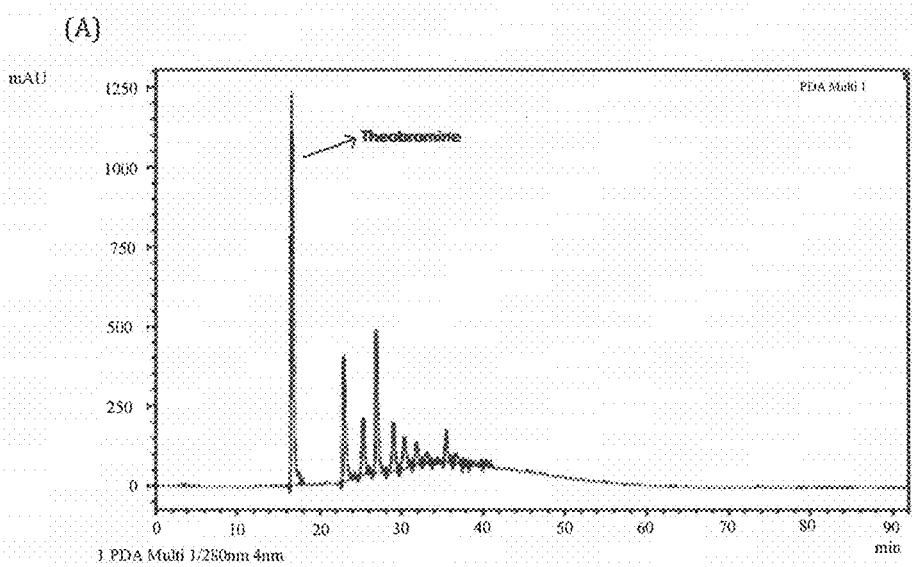

(B)

| Compound Name | Fermented Cocoa (mg/g) | Unfermented Cocoa (mg/g) |
|---|---|---|
| Polyphenol content (UV) | 953.0 | 948.0 |
| Theobromine | 47.7 | 51.0 |
| Caffiene | 13 | 17 |
| Epicatechin (EC) | 255.1 | 259.3 |
| Catechin | 65.8 | 71.3 |
| Procyanidin B2 | 110.1 | 117.3 |
| Trimer | 84.4 | 86.3 |
| Tetramer | 67.1 | 69.5 |
| Pentamer | 61.6 | 73.2 |
| Hexamer | 31.7 | 39.9 |
| Heptamer | 17.7 | 16.9 |
| Octamer | 13.9 | 14.0 |
| Nonamer | 11.0 | 11.3 |
| Decamer | 8.1 | 8.4 |

| Compound Name | Fermented Cocoa (mg/g) | Unfermented Cocoa (mg/g) |
|---|---|---|
| Polyphenol content (UV) | 730.1 | 733.3 |
| Theobromine | 7.1 | 5.5 |
| Caffiene | 2.0 | 2.1 |
| Epicatechin (EC) | 115.9 | 128.3 |
| Catechin | 66.9 | 67.6 |
| Procyanidin B2 | 87.9 | 89.5 |
| Trimer | 49.0 | 53.3 |
| Tetramer | 24.3 | 21.6 |
| Pentamer | 29.0 | 31.6 |
| Hexamer | 19.6 | 17.8 |
| Heptamer | 14.4 | 19.3 |
| Octamer | 9.9 | 11.0 |
| Nonamer | 4.1 | 4.4 |
| Decamer | 2.1 | 2.3 |

Figure 6: HPLC-Fluorescence profile of cocoa procyanidins from monomer to decamer of (A) Crude acetone/water extracts of cocoa beans (B) its percentage composition

Figure 6(A)

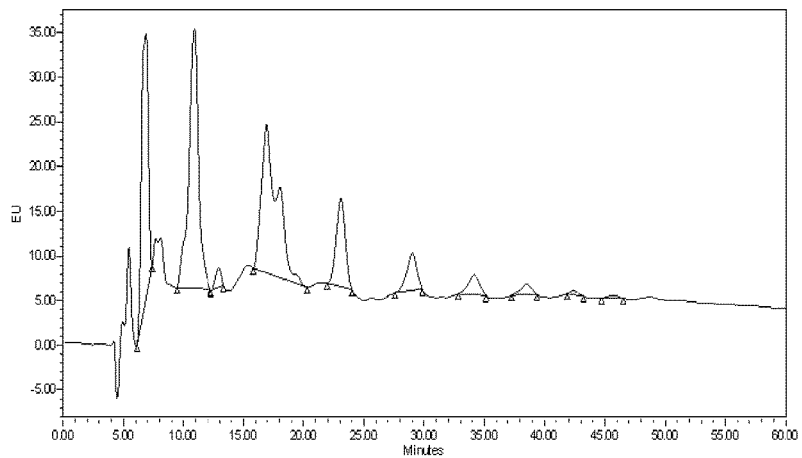

Figure 6(B)

| Compound Name | Fermented Cocoa (mg/g) | Unfermented Cocoa (mg/g) |
|---|---|---|
| Polyphenol content (UV) | 257.0 | 485.0 |
| Theobromine | 64.0 | 53.3 |
| Caffiene | 21.1 | 22.0 |
| Epicatechin (EC) | 55.5 | 61.2 |
| Catechin | 27.7 | 33.3 |
| Procyanidin B2 | 25.1 | 31.1 |
| Trimer | 20.0 | 24.5 |
| Tetramer | 16.1 | 19.3 |
| Pentamer | 15.7 | 19.8 |
| Hexamer | 11.3 | 15.5 |
| Heptamer | 7.1 | 11.2 |
| Octamer | 5.1 | 9.9 |
| Nonamer | 2.5 | 3.8 |
| Decamer | 1.4 | 1.7 |

Figure 7: HPLC-Fluorescence profile of cocoa procyanidins from monomer to decamer of (A) procyanidin enriched extracts of cocoa beans (B) its percentage composition

| Compound Name | Fermented Cocoa (mg/g) | Unfermented Cocoa (mg/g) |
|---|---|---|
| Polyphenol content (UV) | 990.1 | 993.3 |
| Epicatechin (EC) | 275.2 | 279.5 |
| Catechin | 67.8 | 72.3 |
| Procyanidin B2 | 103.1 | 117.3 |
| Trimer | 80.4 | 87.2 |
| Tetramer | 71.1 | 73.5 |
| Pentamer | 71.0 | 73.9 |
| Hexamer | 33.7 | 39.0 |
| Heptamer | 16.7 | 18.9 |
| Octamer | 14.1 | 14.7 |
| Nonamer | 11.0 | 13.3 |
| Decamer | 7.9 | 8.6 |

Figure 8: HPLC-Fluorescence profile of cocoa procyanidins from monomer to decamer of (A) soluble fiber encapsulated cocoa polyphenol containing 30% GAE polyphenol content (B) its percentage composition

Figure 8(A)

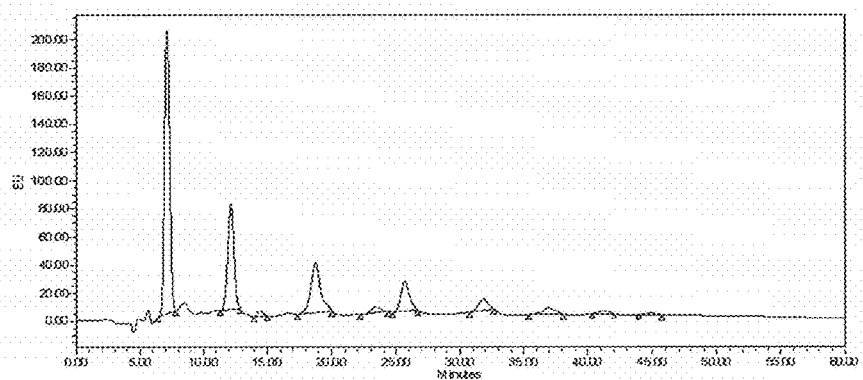

Figure 8 (B)

| Compound Name | Fermented Cocoa (mg/g) | Unfermented Cocoa (mg/g) |
|---|---|---|
| Polyphenol content (UV) | 312.5 | 348.5 |
| Theobromine | 54.2 | 55.0 |
| Caffiene | 22.0 | 23.3 |
| Epicatechin (EC) | 57.5 | 57.9 |
| Catechin | 29.7 | 30.1 |
| Procyanidin B2 | 25.3 | 27.3 |
| Trimer | 17.9 | 18.6 |
| Tetramer | 14.3 | 16.3 |
| Pentamer | 11.1 | 11.9 |
| Hexamer | 10.6 | 13.0 |
| Heptamer | 7.5 | 7.9 |
| Octamer | 4.1 | 5.5 |
| Nonamer | 2.0 | 2.2 |
| Decamer | 1.1 | 1.7 |

Figure 9: (A) Procyanidin enriched cocoa extract impregnated chocolates (400 mg/20g chocolate) (B) commercially available dark chocolate containing 60% cocoa content.

Figure 10: Scanning electron micrograph of cocoa soluble fiber encapsulated cocoa polyphenols
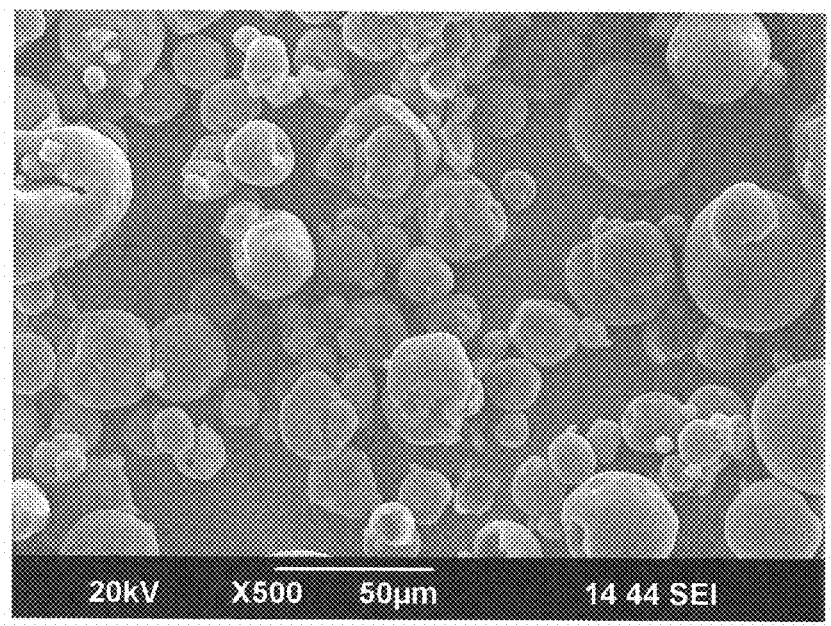

Figure 11: Particle size analysis of cocoa soluble fiber encapsulated cocoa polyphenols powder in water at pH 2, gastric fluid conditions
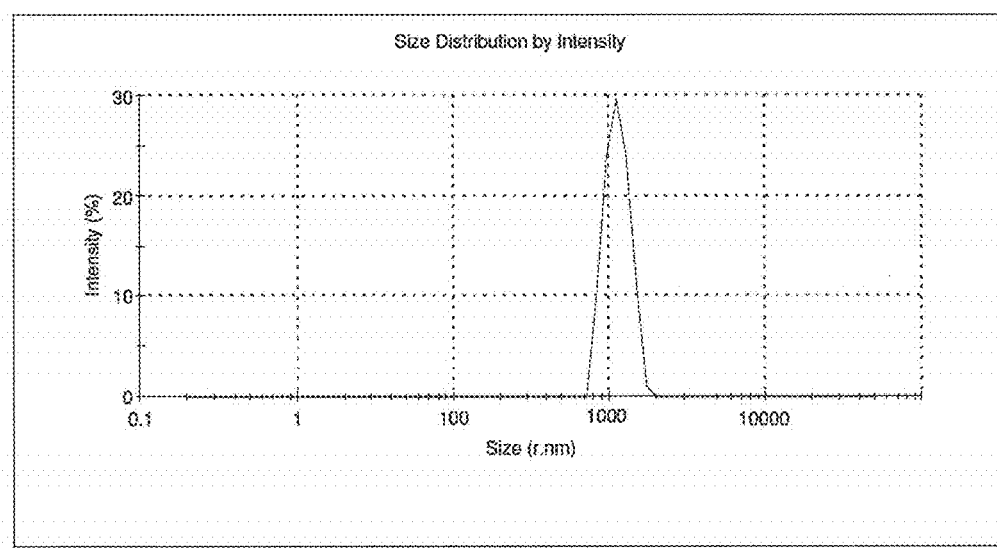

Figure 12: Effect of soluble fiber encapsulated cocoa polyphenols upon the Biochemical & Lipid profile of fatty diet-induced hyperlipidemic wistar rats. HDL-high density cholesterol, LDL - low density cholesterol; VLDL – very low density cholesterol
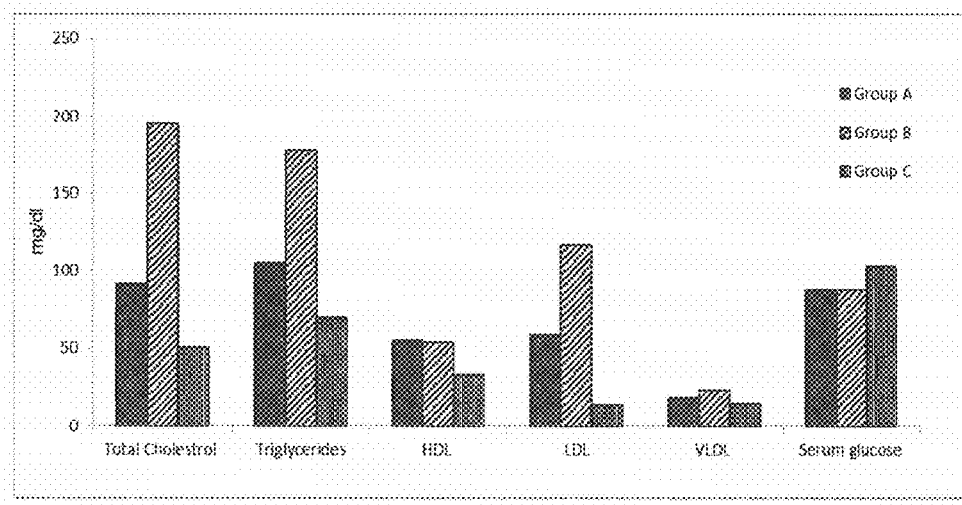

ULTRASOUND-ASSISTED CONTINUOUS EXTRACTION FOR COMPLETE FRAGMENTATION OF COCOA BEANS INTO FRACTIONS

FIELD OF INVENTION

The invention is a novel ultrasound-assisted process for efficient and cost effective production of various commercially significant value-added products with zero waste—'green process', from both fermented and unfermented type of cocoa beans and a state-of-the-art plant facility for executing automatic operations of ultrasonication during continuous and/or batch extractions and homogenization. The extracted value-added fractions rich in cocoa derived phytonutrients were formulated with each other into stable ready use functional ingredients. Various food/beverages incorporating such valuable ingredients also provided as the proof of concept.

BACKGROUND OF THE INVENTION

Cocoa beans (*Theobroma Cacao* L) are one of the most important cash crops around the world. The process for commercial consumption of cocoa begin with the most important postharvest operation of fermentation where the ripened cocoa beans with their surrounding pulp are removed from the pods and placed in piles or bins, allowing access to microorganisms for fermentation. The duration of fermentation may last even seven days to generate unique flavor precursors which eventually provide familiar chocolate taste upon drying. Drying is conventionally performed by spreading the beans out in the sun from five to seven days. The dried beans are cleaned, roasted, and graded. Subsequently the shell of each bean is removed by the process called winnowing to extract the nib. The nibs are ground and liquefied, resulting in pure chocolate in fluid form, referred to as chocolate liquor. The liquor can be further pressed into two components, viz. cocoa solids or pressed cake and cocoa butter. The pressed cake is again processed for adjusting the pH (if required) and powdered to cocoa powder, which is normally the cocoa ingredient for the most majority of cocoa based food products. A large number of patents have been published on specific processes by which fermented cocoa beans can be converted to cocoa powder with unique taste and aroma.

Cocoa beans are very nutritious and contain chockfull of antioxidants, dietary fiber and proteins. On an average, cocoa beans contains 50 to 60% fat, 14 to 16% proteins, 16 to 20% dietary fiber, 5 to 8% carbohydrates and phytochemicals such as polyphenols (4 to 10%), theobromine (1 to 2%), caffeine (0.5 to 1%) etc. Upon fermentation, the carbohydrate profile and polyphenol load decreases. For instance, the polyphenol content of fermented cocoa is less than 3%, as compared to unfermented dried cocoa beans (7 to 9%). Further processes for the production of cocoa powder such as drying, roasting, grinding, alkalization etc are proved to reduce the polyphenol load to less than 1%. Thus, it has been estimated that, more than 80% of the antioxidant phytonutrients, mainly polyphenols belonging to the flavanoid family, especially the flavan-3-ol monomers, (−)-epicatechin and (+)-catechin and several procyanidin oligomers built upon these monomeric units are getting destroyed during the process of cocoa powder manufacture (Kim and Keeney. 1984; Hansen et. al. 1998). Moreover, some considerable fraction of flavonoids are converted to insoluble forms by the action of polyphenol oxidase, which are very poorly bioavailable upon consumption.

The preservation or enhancement of cocoa flavonoids is of great importance since these compounds are found to offer many health beneficial effects. Cocoa polyphenols have been reported to be good antioxidant with greater activity than tea and red wine polyphenols (Lee et al 2003). They are reported as general cardioprotective with wide range of biological activities, including eicosanoid synthesis modulation, increasing nitric oxide synthesis, lowering low-density lipoprotein oxidation, inhibiting platelet activation, stimulation of the production of anti-inflammatory cytokines, and inhibition of the production of certain proinflammatory cytokines etc. Its positive effects in various other disease states such as hypertension, brain function, blood sugar management, body weight management etc have also been substantiated. The skin benefits includes general improvements in skin health such as increased firmness, increased elasticity, reduced wrinkles (including wrinkle width and/or volume), reduced fine lines, increased hydration, decreased skin roughness, decreased scaling, improved skin smoothness, improved skin structure etc. (Waterhouse et al., 1996; Kondo et al., 1996; Mao et al., 1999; Karim et al., 2000; Mao et al., 2000; Rein et al., 2000; Schramm et al., 2001; Wan et al., 2001).

Various solvent systems have been recommended for extraction of polyphenols. Zieglader et al. used methanol to extract the polyphenols from cocoa beans at ambient temperature. The extract was found to contain monomer tannin precursors (catechins, anthocyanidins and their soluble condensates), and used as an additive for oil to preserve from oxidation (See "*Antioxidative effects of cocoa*", *Rev Choc Confect Bak*, 8: 3-6, 1983). Griffiths et al. used methanol extracts of ripe cocoa nibs, again obtained at ambient temperatures, for characterization of polyphenols in cocoa and other plants (*Biochemical J.* 74: 362-365, 1960). Rigaud et al. made extracts from lyophilized cocoa beans and grape seeds, and noted that the use of methanol as a solvent precluded the presence of the higher oligomers (*J. Chromatography* 654:255-60, 1993). Jalal & Collin prepared extracts from different parts of the cocoa plant in order to analyze the polyphenols present in each part of the plant. The extraction was carried out using 70% cold methanol, followed by ethyl acetate (*Phytochemistry*, 16:1377-1380, 1977). Acetone/water has also been used for cocoa bean extractions. Clapperton et al. reported the extraction of defatted cocoa powder made from fermented cocoa beans using cold 70% v/v acetone/water (Polyphenols and Cocoa Flavor, Groupe Polyphenols, XVI. sup Intern. Conf., Lisbon, Portugal, Jul. 13-16, 1992).

Many methods employing above solvents and their optimized ratios and extraction conditions such as temperature, pressure etc have also been patented for the isolation of polyphenols from cocoa beans. Below listed prior arts describe various processes for the isolation of polyphenols, mainly flavonoids consisting flavan-3-ols and procyanidin oligomers from cocoa beans and their uses. The prior arts in concentrating polyphenols generally involves harvest of ripened cocoa fruit, special treatment to inhibit polyphenoloxidase enzyme, drying without fermentation and subsequent solvent extraction under controlled conditions to obtain extracts of original composition endowed with very useful properties.

1. 2008/0193629 A1 reports a water/alcohol or water/acetone extraction of defatted unfermented cocoa beans and further purification of resulting aqueous extracts using microfiltration with molecular weight cut off membranes followed by ultrafiltration and nano filtration to enrich polyphenols to 80% level. The patent is specific for the preparation of polyphenol enriched extracts from unfermented cocoa beans containing higher polyphenol content. It does not say anything about the recovery and process from fermented cocoa beans containing relatively low amount of polyphenol content. The process include separate defatting step using solvents like hexane and also generate more than 90% of the defatted cocoa material as a waste. The process of the invention also requires expensive plant/equipment's installations for the production.

2. U.S. Pat. No. 6,627,232 B1, describes extraction of defatted, unroasted, unfermented cocoa beans with organic solvents such as hexane, acetone, methanol, ethyl acetate etc and their aqueous combinations at various percentage. Extraction solvent systems and conditions such as temperature and pH were optimized to obtain lower molecular weight procyanidin enriched extracts and higher molecular weight procyanidin rich extracts separately. The patented invention has used counter-current batch extraction process. This patent is also specific for the preparation of procyanidin oligomers enriched extracts from unfermented cocoa beans containing higher polyphenol content and does not say anything about the recovery and process from fermented cocoa beans containing relatively low amount of polyphenol content. The process include separate defatting step using solvents like hexane and also generate more than 90% of the defatted cocoa material as a waste. Though the invention has detailed several solvent systems for the extraction of procyanidin oligomers, it does not say anything about the possibility of use of techniques such as ultrasonication or enzymes for the quantitative extraction of useful phytochemicals such as polyphenols and methylxanthines. The invention does not say anything about the process conditions or steps to be followed to make use of the spent of cocoa beans after extracting the procyanidins and methylxanthines to useful ingredients such as dietary fiber, proteins etc. The advantage of the present invention is that it is a green process of ultrasound mediated direct extraction of cocoa beans for highly efficient extraction, purification and formulation of cocoa phytonutrients and the optimized process for the recovery of useful ingredients like dietary fiber, proteins etc, leaving absolutely no waste.

3. U.S. Pat. No. 7,368,144 B2/2008 describes a method for obtaining cocoa bean polyphenol extracts from fresh beans and resulting extracts and uses thereof. It suggests various solvent systems of extraction and compositions comprising polyphenols, xanthins and lipids. The method does not provide any analysis or the characterization of the product in terms of procyanidines and the purity of polyphenol. The patent only describes a method of making a crude extract such as oleoresins and its analysis with respect to fatty acid, phytosterol, polyphenol and xanthines and some cosmetic effect of the said extracts. It does not give any information or analysis of total polyphenols, procyanidines and the recovery of the active ingredient in the process. The patent also does not provide any procedure for enhancing the purity of the phytonutrients such as polyphenols or methylxanthines. Since polyphenols are proved to be an important group of active principles in cocoa beans, higher purity is useful for reducing the dosage and enhancing the activity and also for various formulations with enhanced solubility, stability and bioavailability, for functional food or dietary supplement applications. Moreover, the patent does not provide conditions to make use of the spent of the polyphenol extract as value added fractions of dietary fiber, proteins etc.

4. US2008/0021227 A1 describes the isolation of polyphenols containing procyanidines and their use as antineoplastic agents in cancer treatment. This is a lab scale isolation method in which chlorinated solvents like chloroform are used. In addition, extensive separation of procyanidines using reverse phase and normal phase chromatography and sephadex separation are used. The process does not have any commercial validity as it is a small scale process.

5. US 2007/0134400 A1 details about the fractionation of cocoa beans into various fractions such as butter, cocoa solids, cocoa liquor etc and the polyphenol analysis of each fraction. A number of food recipes for polyphenol incorporation were also suggested. But, the procedure given is only for the selective extraction of procyanidines from specially processed unfermented cocoa beans and does not say anything about the possibility of extraction from normal fermented cocoa beans used for majority of the cocoa based applications or to make cocoa powder. Only small batch scale extraction procedure was given and does not speak about either the possibility of continuous extraction, or the use of techniques like ultrasonication to improve the speed, yield and purity of the extracts. The patent does not mention about the other useful components in cocoa beans such as methylxanthines, dietary fiber or proteins.

6. US 2008/0051587 A1 is basically an existing method with enhanced results (a counter current organic solvent extraction) for the selective extraction of procyanidines. Parameters like temperature, pH, solvent etc are optimized for monomer and oligomer enriched extracts. ie, selective extraction of oligomers according to size have been reported and were analysed by HPLC. However, no data regarding the yield or the purity level of procyanidines have been given. Theobromine levels in the extract were also not mentioned.

7. US 2008/0193629A1 is a patent for a method that details a blanching step of cocoa beans to reduce polyphenol oxidase activity, followed by defatting and extraction with aqueous alcohol or acetone. The extract was further subjected to ultrafiltration, nanofiltration and microfiltration to get the polyphenol enriched extract. The patent suggested the use of supercritical carbondioxide extraction, hydraulic press and solvent extraction to remove fat or butter. The defatted fractions are extracted and subjected to membrane filtration to get the polyphenol enriched extract. Composition of the final product with respect to polyphenol, procyanidines, and theobromine are not mentioned here also.

8. US 2004/096566 is a process for carrying out the extraction under specific conditions that makes it possible to process cocoa beans to provide products with a high polyphenol content enriched (in comparison to the initial content of the beans) with certain useful lipid derivatives. The process use fresh beans, not having undergone a pre-treatment or defatting, having had their pulp and shell removed, in such a way as to obtain clean kernels. The grinding of said kernels in the presence of a solvent, the maceration of the ground kernels under conditions allowing the desired compounds to be extracted, the filtration of the maceration mixture, and the recovery of the extract containing said compounds from the filtrate.

9. US 2010 062138 is a method of selective adsorption of polyphenols on an adsorbent resin, using isopropanol as the solvent to make, cocoa extracts with 90% polyphenol content. Though the patent has quantified the polyphenol content, nothing is mentioned about the theobromine levels in the final product. It is also specific for unfermented cocoa beans having high levels of polyphenols and was blind about the fiber and proteins recovery, the method of application to fermented cocoa beans etc.

The limitation of all the prior arts is that they all use specially processed unfermented or under fermented cocoa beans. The processes in the prior arts are not efficient enough to quantitatively isolate water soluble polyphenols from fermented cocoa beans containing relatively low amounts of polyphenols as compared to the unfermented cocoa beans. The fermented cocoa beans are rich in water insoluble procyanidins, which makes the prior art processes difficult. Pre-treatment of cocoa and its post-harvest operations for overcoming this difficulty constitute a major drawback, as it destroys the active healthy polyphenols of cocoa beans. This also makes the commercial extraction of polyphenols from common fermented cocoa beans difficult or even impossible. The prior arts isolate only one value added fraction, namely polyphenols or flavonoids of cocoa beans and leaves more than 90% (w/w) of cocoa beans as waste. None of the prior art provides a complete fractionation of the cocoa beans into value added products to utilize the whole components of cocoa as valuable products.

The present invention overcomes the limitations in the prior arts and is a 'Green process'. The present invention also utilizes the waste after solvent extraction for making various value added products and also minimizes the use of organic solvents like hexane.

The prior art methodologies include multi solvent extraction methods designed for batch wise processes, essentially including initial defatting process of hexane extraction or supercritical fluid extraction followed by drying of cocoa residue and further polyphenol extraction with aqueous mixture of polar organic solvents. The disadvantage of the prior art is that these methods lack the integrity due to the use of class I solvents like hexane, which are not preferred in the manufacture of food ingredients and dietary supplements. Drying of hexane defatted cocoa beans is difficult in a commercial scale, as normal drying method using steam jacket, or electrical heating will damage the polyphenol content and cause colour change and aroma change due to the presence of various phytochemicals such as amines, fat, polyphenols etc. Yet another disadvantage associated with the prior arts is that the relative percentage of methylxanthins, especially theobromine and caffeine content of the isolated polyphenol rich extracts is not reported in many cases and hence it is not possible to develop methods for controlling their levels in the isolated polyphenol-rich extracts. All these prior arts consider only the subject compound leaving the majority of the other phytonutrients as waste.

The prior arts U.S. Pat. No. 6,627,232, U.S. Pat. No. 5,554,645, U.S. Pat. No. 4,390,698, U.S. Pat. No. 4,407,834, U.S. Pat. No. 4,755,391, U.S. Pat. No. 4,444,798, U.S. Pat. No. 4,755,391, U.S. Pat. No. 4,904,773, WO 2010/066015 A2, U.S. Pat. No. 1,073,441, U.S. Pat. No. 1,855,026, U.S. Pat. No. 1,925,326, U.S. Pat. No. 4,755,391, US 2003/0170199 A1 and US 2004/103334A1 were dealing with the extraction and purification of another group of phytonutrients called methylxanthines, especially theobromine present in cocoa beans. These prior arts dealing with the extraction and purification of methylxanthines, were mainly carried out in fermented cocoa beans and are very specific for the desired compound, leaving more than 90% of cocoa solids containing valuable dietary fiber and proteins as waste. Some prior arts have not accounted for the valuable antioxidant polyphenol load, while isolating the methylxanthines. The advantage of the present invention over these prior arts is that it provides a unique method for the quantitative extraction and purification of theobromine from cocoa beans, while allowing the complete fractionation of cocoa beans into other useful products such as cocoa polyphenols, dietary fiber, proteins etc. Further, the recovery of methylxanthines has been tremendously improved by using the technique of ultrasonication in commercial level.

Though many patents have been listed for the preparation and usefulness of other constituents of cocoa beans such as proteins, there is no prior art suggesting a green process for the complete fractionation of cocoa beans into commercially significant value-added products for food ingredient, functional food ingredient, nutraceutical, and/or cosmeceutical use. The present invention attempts to overcome the limitations of the prior arts and relates to a novel extraction method based on ultrasound technology employing enzymes, for the quantitative conversion of cocoa beans into various value-added ingredients. A state-of-the-art plant facility for executing the said process of ultrasound assisted continuous extraction and fractionation of extract into various value-added products in commercial scale was also provided. PLC—(Programmable Logic Controller) based ultrasonication was developed for automation of the process at controlled temperature. The present invention deals with specific conditions for such extractions and use of enzymes in such extractions for enhancing the recovery of active ingredients such as polyphenols from cocoa beans.

An advantage of the present invention is that it relates to a novel extraction method based on ultrasound technology employing enzymes, for the quantitative conversion of cocoa beans into various value-added functional ingredients and a total state-of-the-art plant facility for executing the process in commercial scale, and continuous manner with PLC-based ultrasonication at critical steps such as initial cocoa beans extraction and soluble dietary fiber extraction. Ultrasonication at critical steps helps for efficient extraction of phytochemicals such as polyphenols and methylxanthines, with more than 95% recovery. The invention also has the advantage in that the process can be applied to both fermented, unfermented or under fermented cocoa beans for quantitative isolation of available phytonutrients. Ultrasonication also helps the direct extraction of cocoa beans without prior defatting processes like hexane extraction or mechanical expulsion or supercritical extraction or the like, which usually form an important step in all the prior arts. The use of various enzymes in combination with ultrasonication helps for the efficient extraction and preparation of soluble dietary fiber in high yield and purity.

Another advantage of the present invention over the prior arts was that it has used various enzymes in combination with ultrasonication for the efficient extraction and preparation of soluble dietary fiber from cocoa nibs, in high yield and purity.

Yet another advantage of the present invention over the prior arts is that the present process can avoid use of multiple solvents and total extraction of phytonutrients can be achieved on non-defatted cocoa beans.

A further advantage of the present invention over the prior arts is that better purity and extraction yield and fast cycle time are achieved.

Still another advantage of the present invention over the prior arts is that the present process can be automated for selective application of ultrasound at various stages of operations, resulting in the continuous production of various cocoa beans involving minimum labour and cost.

Another advantage of the present invention over the prior arts is that various products are produced simultaneously and continuously and the total design of a plant facility for such a production of various value added products is achieved.

A further advantage of the present invention over the prior arts is that the present process uses simple water based ion exchange and adsorption chromatography for the purification and recovery of phytonutrients like polyphenols and methylxanthins in single operations.

Yet another advantage of the present process is to make various grades of methylxanthins and its unique compositions with epicatechin by selectively eliminating higher oligomeric procyanidins, using a liquid-liquid extraction process. Epicatechin is regarded as one of the efficient bioavailable antioxidant polyphenol belonging to flavan-3-ol widely distributed in cocoa and many other plants.

Another advantage of the present invention over the prior arts is that the residue of cocoa nibs left after cocoa flavor and polyphenol extraction is further processed to dietary fiber rich in proteins with unique flavor suitable for using in cocoa or chocolate based food products.

Still another advantage of the present invention over the prior arts is that the present process can produce high yield and purity, not less than 70% of cocoa soluble dietary fiber from the residue of cocoa nibs left after cocoa flavor or phytonutrients extraction. High soluble fiber content helps to reduce the dosage and easy incorporation into various food stuffs at physiologically significant dosages per serving. Moreover, higher the purity of the fiber, higher will be its neutral organoleptic character, such as taste and flavor/aroma. Consumption of physiologically significant amounts of soluble fiber helps to reduce cholesterol levels, blood sugar levels, for satiety, to reduce hunger etc.

Yet another advantage of the present invention over the prior arts is that cocoa nibs derived soluble dietary fiber is employed for the encapsulation of cocoa polyphenols to enhance the stability, solubility and bioavailability. Being a soluble dietary fiber derived from cocoa, it can be used as a very safe fiber supplement in all cocoa or chocolate containing food items. It can be used as a replacement for many other excipients/additives like starch, hydroxypropylmethylcellulose, and other thickeners, hydrocolloids and binders like guar gum, gum *acacia* etc. Being a byproduct in cocoa polyphenol or cocoa flavor production, it becomes cost effective. It also provides a unique way of preparation of antioxidant dietary fiber or dietary fiber possessing good antioxidant properties for dietary supplement applications.

A further advantage of the present invention is that it provides a state-of-the-art plant facility where by cost effective commercial scale continuous process of extraction of cocoa beans can be performed by employing PLC-controlled automatic ultrasonication for fast and efficient extraction.

Yet another advantage of the present invention is that it provides a methodology for applying ultrasound waves to a continuous extractor and batch extractor for enhancing the efficiency of botanical extractions.

Another advantage of the present invention is that it efficiently uses ultrasonication for efficient extraction of phytochemicals such as polyphenols and methyxanthines from lipid rich plant seeds such as cocoa beans.

OBJECT OF THE INVENTION

An object of the present invention is the development of an automatable plant facility capable of executing the various processes for deriving a set of commercially important value-added products, from both fermented and non-fermented and under fermented varieties of cocoa beans and other botanicals.

Another object of the present invention is to develop a zero waste green process for fractionation of cocoa beans into various commercially significant fractions.

Yet another object of the present invention is to develop a novel and efficient process of cocoa beans extraction using ultrasonication and enzymes to get enhanced recovery and purity of phytochemicals such as polyphenols, methylxanthines and soluble dietary fiber.

A further object of the present invention is to develop a suitable state-of-the-art ultrasound mediated PLC-based automatic plant facility, meeting the global safety and quality regulations, for continuous production of the various value-added cocoa beans derived phytonutrients.

Still another object of the present invention is to develop a process for the direct single step quantitative extraction of phytochemicals such as polyphenols, methylxanthines etc from fat rich plant materials such as cocoa beans with the help of ultrasonication, avoiding conventional separate defatting step.

An object of the present invention is to propose a new ultrasonication method for the preparation of cocoa extract with a unique composition containing not less than 980 mg/g (w/w) polyphenols enriched with not less than 700 mg/g procyanidines and methylxanthins from cocoa beans, with an overall extraction efficiency not less than 95%.

An object of the present invention is to propose a new ultrasonication method for the preparation of cocoa extract with a unique composition containing not less than 950 mg/g polyphenols enriched with procyanidines and low methylxanthin content, not more than 0.1% (w/w) from cocoa beans, with an overall extraction efficiency not less than 95% as de-theobrominated cocoa flavonoids.

Yet another objective of the present process is to develop a liquid-liquid extraction process for the preparation of methylxanthins (theobromine and caffeine) and its unique composition with epicatechin by selectively eliminating higher oligomeric procyanidins as water soluble extracts.

Another advantage of the present process is to prepare 300 to 500 mg/g theobromine containing extracts as water soluble powder. Chemical synthesis of theobromine and its insolubility in water makes assumes the significance of the present extraction from cocoa beans for functional applications.

A further object of the present invention is to derive cocoa dietary fiber and cocoa soluble dietary fiber from cocoa nibs after extracting the flavor and phytochemicals Another object of the present invention is to drive unique composition of dietary fiber and proteins, containing not less than 50% w/w of total dietary fiber and 25% w/w of proteins from cocoa nibs, for various dietary applications Still another object of the present invention is to drive unique composition of soluble dietary fiber and proteins, containing not less than 70% w/w of total dietary fiber and 15% w/w of proteins from cocoa nibs, for various dietary applications Another objective of the present invention is to derive cocoa proteins and cocoa protein hydrolysates from cocoa residue for functional applications An object of the present invention is to provide a methodology by which ultrasonication can be conveniently and automatically applied to a continuous and batch solvent extractor and a mechanism for the same.

A further object of the present invention is to develop a novel ultrasound mediated enzymatic process for the high purity and high yield extraction of cocoa soluble fiber with 70 to 90% purity and to formulate antioxidant dietary fiber which contain physiologically relevant concentrations of polyphenols Still another object of the present invention is to provide cocoa soluble dietary fiber encapsulated cocoa flavonoids with enhanced stability, solubility, antioxidant effect and bioavailability and a process for making the same Yet another objective is to derive non-hygroscopic cocoa soluble dietary fiber as an effective encapsulating agent for hygroscopic plant extracts such as cocoa polyphenols Another object is to develop a green process employing only water and ethyl alcohol for the production of cocoa derived water soluble procyanidin oligomers with more than 95% purity, for nutraceutical applications, which are reported to have high bioavailability.

Yet another objective of the present invention id to prepare water soluble cocoa flavor with characteristic smell of chocolates for food applications

SUMMARY

The present invention relates to a novel ultrasound mediated 'Green' process for efficient and cost effective production of various commercially significant value-added products from cocoa beans with zero waste and a state-of-the-art plant facility for executing automatic operations of ultrasound mediated extractions for fast and efficient extraction is presented in the present invention. The present invention is a unique process of zero waste where complete fractionation of cocoa beans, including both fermented and unfermented type, into for various value added products of significance was achieved by aqueous, hydro-alcoholic and hydro-acetone extractions mediated by ultrasonication-assisted enzymatic treatment. The invention also provides a novel methodology for providing high energy ultrasound cavitations for a continuous extraction where material to be extracted is in contact with the solvent under controlled temperature conditions.

The various plausible products that can be produced in the present process includes high purity (95%) water soluble cocoa polyphenols containing highest levels of flavan-3-ols and not less than 70% procyanidin oligomers, de-theobrominated cocoa polyphenols with less than 0.1% w/w of methylxanthines (theobromine and caffeine), unique composition of methylxanthins, especially theobromine enriched epicatechins by selectively eliminating higher oligomeric procyanidins, cocoa dietary fiber containing high levels of proteins, unique composition of soluble dietary fiber and proteins from cocoa nibs, soluble fiber encapsulated cocoa polyphenol with greater stability and bioavailability, cocoa flavour and various combinations thereof.

In one aspect, the present disclosure provides a process for the complete fractionation of cocoa beans with 'zero waste' into various value-added ingredients of functional use for food/dietary supplement/cosmetic applications which comprises the steps of, a) Cutting, flaking and powdering of dried cocoa beans (fermented or unfermented or partly fermented) and their ultrasound aided extraction with aqueous admixture of polar organic solvents such as lower aliphatic alcohols or lower aliphatic ketones, filtering and evaporating the solvent extract under reduced pressure to obtain a concentrate rich in polyphenols, procyanidins, theobromine, and other phytochemicals present in cocoa beans with an overall recovery of not less than 95% w/w b) Further evaporation of the concentrate mentioned under 1(a) at greater than 100° C. for 3 to 6 h and blending with emulsifiers such as sugar syrup, glycerol, propylene glycol or the like to produce dark free flowing viscous liquid with characteristic smell of chocolate/cocoa flavor as food/beverage ingredient c) Evaporation and concentration of the alcohol-water or ketone-water extract of cocoa mentioned in 1(a) to a dissolved solid content of 5 to 20%, chromatographically separating said dried extract, eluting the column with lower alcohols and acetone either alone or in combination with water, evaporating this element under vacuum to obtain a free flowing procyanidin type B polymer-rich polyphenolic extract (>980 mg/g polyphenols) rich in procyanidins (>700 mg/g) and methylxanthins (>40 mg/g) with an overall recovery of not less than 95% w/w d) Evaporation and concentration of the alcohol-water or ketone-water extract of cocoa mentioned in 1(a) to a dissolved solid content of 5 to 20%, chromatographically separating said dried extract, eluting the column with lower alcohols and acetone either alone or in combination with water, evaporating this element under vacuum to obtain a free flowing procyanidin type B polymer-rich polyphenolic extract (>95% polyphenols) free from the methylxanthines such as caffeine and theobromine inherently present in cocoa beans. Further spray drying or freeze drying can provide methylxanthin-free water soluble cocoa polyphenols rich in procyanidins as water soluble powder with an overall recovery of not less than 95% w/w.

e) Collection and concentration of the column wash as specified under 1(d) and its evaporation and extraction with ethyl acetate followed by partition with acidified water to produce water soluble theobromine-rich powder (300 mg/g to 500 mg/g)

f) Evaporation of the alcohol-water or acetone-water extract obtained by the ultrasound aided extraction of cocoa beans and further partition with ethyl acetate followed by further extraction of ethylacetate layer with acidified water to produce cocoa methylxanthins rich in theobromine (300 to 500 mg/g) and caffeine (70 to 100 mg/g) containing epicatechin (70 to 100 mg/g) as water soluble powder, by selectively eliminating higher oligomeric procyanidins g) Drying the residue left after solvent extraction in claim 1(a) under vacuum to produce a unique composition of de-bittered dietary fiber and proteins of cocoa suitable for food applications f) Further ultrasound aided enzymatic extraction of the total dietary fiber of cocoa obtained in claim 1(e) to selectively extract the soluble dietary fiber of cocoa beans h) Digesting the protein rich cocoa dietary fiber obtained in step 1 (g) with alkaline solution (at pH 10 to 12), centrifugation and acidification of the supernatant solution to pH 3 to 4 with dilute mineral acids such as hydrochloric acid to precipitate cocoa beans proteins followed by its pH adjustment and further membrane filtration and spray drying to get cocoa proteins containing not less than 70% protein content.

i) Treatment of the proteins obtained under claim 1(g) with proteases under ultrasonication followed by spray drying to provide cocoa protein hydrolysates for functional applications j) Preparation of water solution of cocoa polyphenols prepared under 1(d) and soluble fiber prepared under 1(h) separately, and mixing them with or without the other soluble fibers such as gum *acacia*, fenugreek galactomannans etc under high pressure homogenization conditions followed by spray drying to provide unique composition of cocoa fiber encapsulated cocoa polyphenols containing not less than 400 mg/g cocoa polyphenols and 350 mg/g dietary fiber.

In another aspect of the present invention a fully automatic plant facility was provided for the ultrasound assisted continuous extraction of cocoa beans, whereby several tons of cocoa beans can be extracted per day by controlling the temperature to avoid thermal degradation of valuable phytochemicals in cocoa such as polyphenols/procyanidins.

Advantageously, in the present process, the said cocoa beans can be fermented or unfermented or partially fermented can be used for the quantitative extraction of polyphenols/procyanidins and methylxanthines Advantageously, in the present process the said solvent extraction can be carried out directly on cocoa beans that have not undergone defatting process Advantageously, in the present process, the said organic solvent extraction is carried out with a mixture of acetone and water at 60-90% v/v of acetone, or ethanol-water mixture containing 60 to 80% v/v ethanol, at a temperature range of 40 to 50° C., under the action of ultrasonication.

Advantageously, in the present process the crude extract of cocoa beans can be roasted with sugar syrup at 100 to 120° C. for 3 to 6 h to produce a unique chocolate flavor, having a composition of cocoa fat 10 to 20%, carbohydrates 35 to 50%, proteins 15 to 20% . . . and theobromine 3 to 6% w/w, suitable for food/beverage applications Advantageously, in the present process the total polyphenol of the extract is >950 mg/g gallic acid equivalent with procyanidin oligomers (monomer to decamer) ranging from 400 mg/g to 700 mg/g as characterized by HPLC analysis and methylxanthins (as theobromine and caffeine) as 10 to 50 mg/g Advantageously, in the present process polyphenols with greater than 900 and 950 mg/g gallic acid equivalent containing not less than 0.1% w/w theobromine can also be prepared by changing the chromatographic stationary phase as selective adsorbent resins.

Advantageously, the present process provided a unique composition of water soluble theobromine-rich powder, having a composition of 300 mg/g to 500 mg/g theobromine Advantageously, the present invention also provided a liquid-liquid extraction process to produce a unique composition of water soluble theobromine-rich powder, having a composition of 300 mg/g to 500 mg/g theobromine, 70 mg to 100 mg caffeine and 70 to 100 mg epicatechin without higher molecular weight procyanidin oligomers.

Advantageously, in the present process the residue after solvent extraction is dried under vacuum at a temperature below 70° C. to remove imbibed solvents to less than 20 ppm level and powdered to provide a unique composition of tasteless cocoa dietary fiber with mild characteristic flavor of chocolate containing not less than 55% total dietary fiber, not less than 20% proteins, and not less than 15% carbohydrates Advantageously, in the present process the residue of dietary fiber obtained, is treated with enzymes like proteases, amylases and amyloglucosidases and further extracted with water under ultrasound conditions at less than 4 to 6 h and the water extract was concentrated and mixed with alcohol to precipitate the soluble fiber having not less than 70% fiber content.

Advantageously, in the present process the residue of dietary fiber obtained, can be extracted with dilute alkali to obtain water soluble powder containing 60 to 80% (w/w) cocoa bean proteins and can be further treated with proteases to provide cocoa bean protein hydrolysates.

Another embodiment of the present invention is a unique composition of cocoa polyphenols/procyanidins and soluble dietary fiber containing not less than 40% polyphenols and 35% soluble dietary fiber and a process for the same.

According to another embodiment, the present invention provides a stable composition of polyphenols/procyanidins of cocoa obtained by the microencapsulation using soluble dietary fiber-derived from cocoa beans.

According to another embodiment, the present invention provides a water dispersible and sustained release formulation of cocoa polyphenols with cocoa soluble dietary fiber for better bioavailability.

According to another embodiment, the present invention provides a stable composition of cocoa antioxidants having a minimum of 12 months shelf life for blood lipid profile management comprising cocoa polyphenols having not less than 25% polyphenols and 30% soluble dietary fiber.

According to another embodiment, the present invention provides a method for reducing blood cholesterol levels and body weight controlling in mammals comprising the steps of administering an effective of cocoa procyanidine of type B polymers encapsulated in cocoa dietary fiber.

According to another embodiment, the present invention provides a unique composition of cocoa polyphenols/procyanidins with cocoa soluble dietary fiber isolated from cocoa beans as water soluble powder suitable for cosmetic applications due to the uniform emolument, viscous and gummy effect of cocoa fiber suitable for application on the skin as a thin film and can be peeled off as a film after 30 min of application.

The foregoing has outlined some of the most pertinent objects of the invention. These objects should be construed to be merely illustrative of some of the more prominent features and applications of the intended invention. The invention includes other features and advantages which will be described or will become apparent from the following more detailed description of the embodiment.

BRIEF DESCRIPTION OF DRAWINGS

FIG. 2: Schematic representation of ultrasound aided continuous extractor developed for the direct extraction of cocoa beans FIG. 3: Schematic representation of various value-added products derived from cocoa beans with 'zero waste-green process'

FIG. 4: HPLC-diode array profile of cocoa extract with >98% gallic acid equivalent polyphenols (A) with theobromine (B) de-theobrominated polyphenols detected at 280 nm FIG. 6: (A) Procyanidin enriched cocoa extract impregnated (400 mg/20 g chocolate) chocolates (B) normal commercially available dark chocolate containing 50% cocoa content.

FIG. 8: Particle size analysis of cocoa soluble fiber encapsulated cocoa polyphenols powder in water at pH 2, gastric fluid conditions FIG. 10: Scanning electron micrograph of cocoa soluble fiber encapsulated cocoa polyphenols FIG. 11: Particle size analysis of cocoa soluble fiber encapsulated cocoa polyphenols powder in water at pH 2, gastric fluid conditions FIG. 12: Effect of soluble fiber encapsulated cocoa polyphenols upon the Biochemical & Lipid profile of fatty diet-induced hyperlipidemic wistar rats. HDL—high density cholesterol, LDL—low density cholesterol; VLDL—very low density cholesterol

DETAILED DESCRIPTION

Figure 1A:
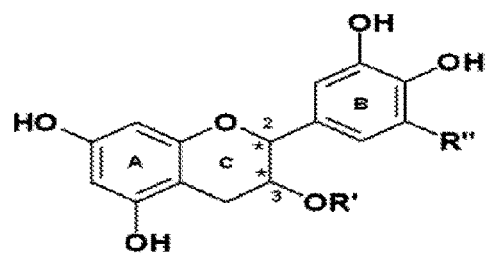
FIG. 1: Representative chemical structure of a procyanidin oligomer with Type A & B linkages.
Figure 1B:
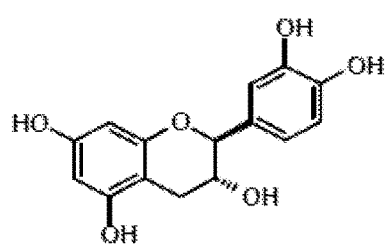

The present invention will now be described more fully herein after. For the purposes of the following detailed description, it is to be understood that the invention may assume various alternative variations and step sequences, except where expressly specified to the contrary. Thus, before describing the present invention in detail, it is to be understood that this invention is not limited to particularly exemplified systems or embodiments that may of course, vary. The use of examples anywhere in this specification including examples of any terms discussed herein is illustrative only, and in no way limits the scope and meaning of the invention or of any exemplified term. Likewise, the invention is not limited to various embodiments given in this specification.

As used herein, the singular forms "a," "an," and "the" include plural reference unless the context clearly dictates otherwise. The term "and/or" means one or all of the listed elements or a combination of any two or more of the listed elements The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value and end-point referred to.

As used herein the terms "comprises", "comprising", "includes", "including", "containing", "characterized by", "having" or any other variation thereof, are intended to cover a non-exclusive inclusion.

The limitation of all the prior arts is that they all use specially processed unfermented or under fermented cocoa beans. The processes in the prior arts are not efficient enough to quantitatively isolate water soluble polyphenols from fermented cocoa beans containing relatively low amounts of polyphenols as compared to the unfermented cocoa beans. The fermented cocoa beans are rich in water insoluble procyanidins, which makes the prior art processes difficult. Pre-treatment of cocoa and its post-harvest operations for overcoming this difficulty constitute a major drawback, as it destroys the active healthy polyphenols of cocoa beans. This also makes the commercial extraction of polyphenols from common fermented cocoa beans difficult or even impossible. The prior arts isolate only one value added fraction, namely polyphenols or flavonoids of cocoa beans and leaves more than 90% (w/w) of cocoa beans as waste. None of the prior art provides a complete fractionation of the cocoa beans into value added products to utilize the whole components of cocoa as valuable products.

The present invention solves the problem of the prior arts by introducing a novel ultrasound-assisted process for efficient and cost effective production of various commercially significant value-added products with zero waste-green process, from both fermented and unfermented type of cocoa beans and a state-of-the-art plant facility for executing automatic operations of ultrasonication during continuous and/or batch extractions and homogenization (FIG. 2, 3). The extracted value-added fractions rich in cocoa derived phytonutrients were formulated with each other into stable ready use functional ingredients.

The processes for the differential extraction of components are described below (FIG. 3).

In one embodiments of the present invention, dried beans containing less than 10% moisture is cut and flaked to 3 to 5 mm thickness flakes and subjected to an ultrasound-mediated continuous extraction using water or admixtures of water and ethanol or acetone containing minimum 20% v/v water at temperature between 50 to 60° C. A continuous extractor was developed by inserting Ultrasound-probes which are always in contact with the solvent used for extraction and the ultrasound generator is fitted with a timer by which sonication and cavitation can be applied as pulses of varying duration, say 1 to 30 min, depending on the extractability (FIG. 2). The PLC—(Programmable Logic Controller) controlled censor can also detect the temperature of the solvent and get automatically stopped when the temperature of the extracting solvent exceeds designated temperature, say 60° C. Ultrasonication can extract total flavours, taste and phytonutrient loads such as polyphenols and methylxanthines of cocoa beans in the continuous extractor leaving the major chunk cocoa spent rich in proteins and dietary fiber. The dried residue thus obtained can further be treated with water at definite pH and temperature conditions with enzymes such as proteases and amylases under conditions of sonication to extract soluble and de-bittered cocoa dietary fiber rich in proteins and exhibiting a unique flavour compatible with various chocolates. The liquid extract containing cocoa extractives (referred to as 'miscella') can be evaporated at 60 to 80° C. to a total dissolved solid level of 15 to 20% (w/v) and blend with sugar syrups etc and food grade emulsifiers such as propylene glycol, polyglyceryl esters of fatty acid etc and further concentrate at 100 to 120° C. for 3 to 6 h to a free flowing brownish liquid, with less than 20 ppm residual solvent level, with characteristic chocolate like aroma and taste suitable for food/beverage applications.

Figures 5, 5B:
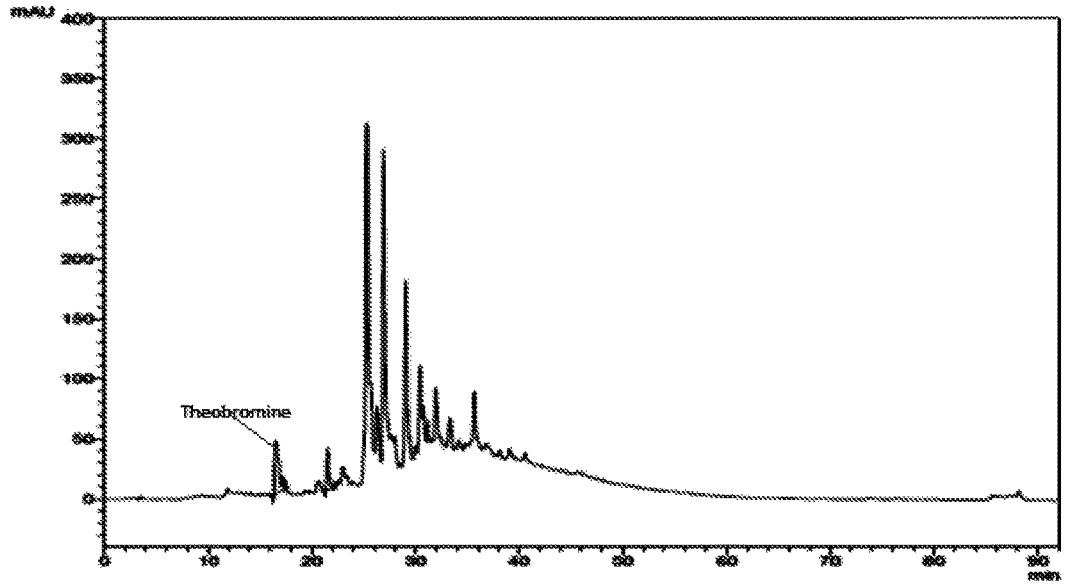
FIG. 5: HPLC-diode array profile at 280 nm (A) de-theobrominated cocoa extract with >95% gallic acid equivalent polyphenol content containing less than 0.1% (W/W) theobromine and (B) its percentage composition
Figures 7A, 7B:
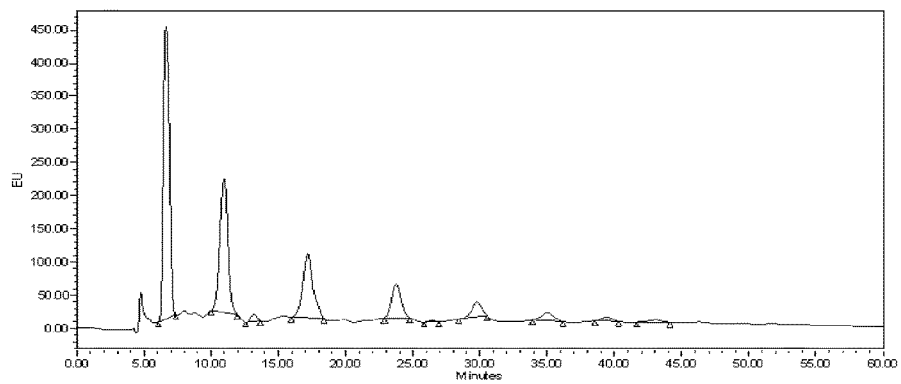
FIG. 7: Scanning electron micrograph of cocoa soluble fiber encapsulated cocoa polyphenols
Figure 9:
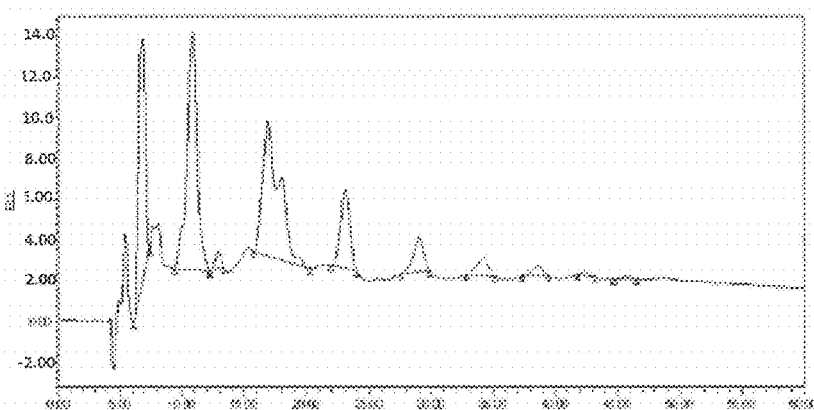
FIG. 9: Effect of soluble fiber encapsulated cocoa polyphenols upon the Biochemical & Lipid profile of fatty diet-induced hyperlipidemic wistar rats
Figure 9B:
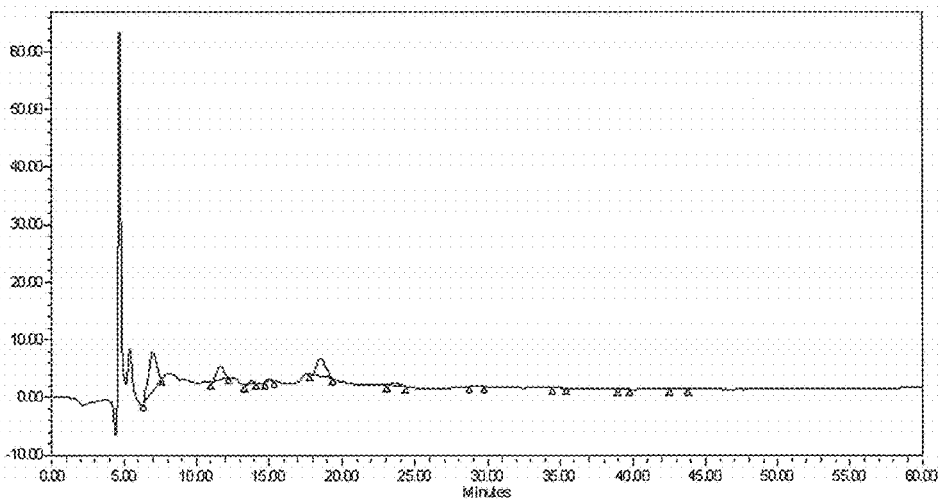

Advantageously, in one aspect of the present invention, the liquid extract containing cocoa extractives (referred to as 'miscella') can be processed alternatively by concentrating at low temperature, less than 45° C. and the concentrated miscella was further subjected to adsorption and/or ion chromatography to isolate polyphenols and methylxanthines to prepare unique compositions of polyphenols with or without methylxanthines. Briefly, the concentrated miscella having 15 to 20% w/v total dissolved solids was concentrated and allowed to settle at low temperature, preferably below 20° C. for 3 to 5 hours and filtered. The filtrate is loaded onto an adsorbent divinyl benzene-crosslinked polystyrene resin column and washed repeatedly with water at 25° C. to 30° C. and then with hot water at 40-50° C. and further with water containing 1 to 3% ethanol. After the washings, column is eluted with ethanol alone or ethanol and water mixture, most preferably 70 to 95% ethanol v/v. The column eluent is collected, evaporated under vacuum or most preferably spray dried to get free flowing polyphenol rich powder containing procyanidin type B polymers, containing monomer to decamer (>70% epicatechin equivalent (FIG. 4), when calculated using HPLC-fluorescence method of Robbins R J et al, Journal of AOAC international, 2012, 95 (4), 1153-1160) and not less than 10% (w/w) of theobromine as per HPLC method of quantification (Hung-Ju Chen et al, International Journal of Molecular Science, 2012, 260-285) Alternatively, the resin can be changed to a polyamide resin and elute the same way as before to selectively remove the methylxanthins from polyphenols to produce cocoa polyphenols (>95%) and methylxantnines less than 0.1% (w/w). (FIG. 5)

In another embodiment of the invention, the dried residue obtained after solvent extraction can further be treated with water at definite pH and temperature conditions with enzymes such as proteases, amylases and amyloglucosidases, either alone or in combination, under conditions of sonication to extract soluble and de-bittered cocoa dietary fiber rich in proteins and exhibiting a unique flavour compatible with various chocolates. The soluble cocoa dietary fiber can then be subjected to ultrasound mediated enzymatic digestion for the isolation of soluble dietary fiber with and without proteins. Ultrasound aided solvent extraction allowed the complete removal of the characteristic bitter taste and fats of cocoa beans to produce tasteless dietary fiber of cocoa; unlike in the common solvent extraction process where the taste and fat will not be able to remove in such an easy manner.

In yet another embodiment of the invention, the combination of soluble dietary fiber and polyphenol concentrate at various relative percentages is subjected to ultrasound-assisted homogenization and spray drying to produce stable, water soluble cocoa polyphenols encapsulated in cocoa soluble fiber matrix, exhibiting enhanced bioavailability (FIG. 8, 10). The resulting microencapsulated cocoa polyphenols was water soluble making particles of 1.0±0.2 µm in aqueous solutions of pH 2.0, simulating gastric fluid conditions (FIG. 11). The resulting microencapsulated cocoa polyphenols were shown to be of stable granular size with 100±20 mesh size, having a tapped density of 0.4 to 0.5 g/mL, free flowing and stable for storage of two years in air-tight sealed containers protected from moisture and sunlight. The powder was also found stable in solutions at 90° C. for 30 min with an average loss of less than 5% polyphenol content, making it suitable for pasteurization process once added in the food/beverages.

According to the present invention a novel method has been developed which allows the selective extraction of bioactive and bioavailable polyphenols and procyanidin oligomers of Type B and methylxanthines (theobromine and caffeine), from various types of cocoa beans (fermented, unfermented or partially fermented) with more than 95% recovery. The process also provides unique ways to de-theobrominate/de-caffenate cocoa polyphenols to less than 0.1% (w/w) levels, using only water and ethanol. The entire process can be carried out to produce organic quality cocoa extract products using only water and ethanol. Aliphatic ketones containing less than five numbers of carbon atoms, lower aliphatic alcohols containing less than five numbers of carbon atoms and/or water alone can also be used for the process.

Advantageously, in one aspect of the present invention, when water alone is used, the extraction needs to be carried out at a temperature ranging from 50 to 90° C. at acidic pH at 4 to 5.5. The product obtained in water soluble, free flowing and directly compressible form was found to contain not less than 98% polyphenol content as Gallic acid equivalent.

Figure 1:
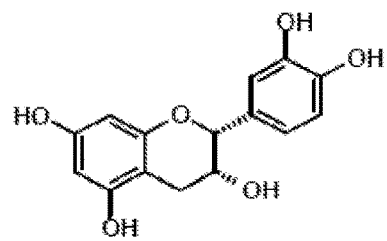
Figure 1D:
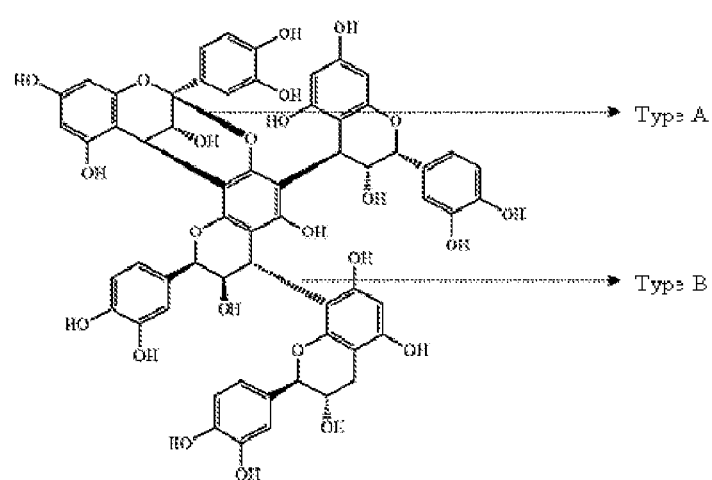
Figure 1E:
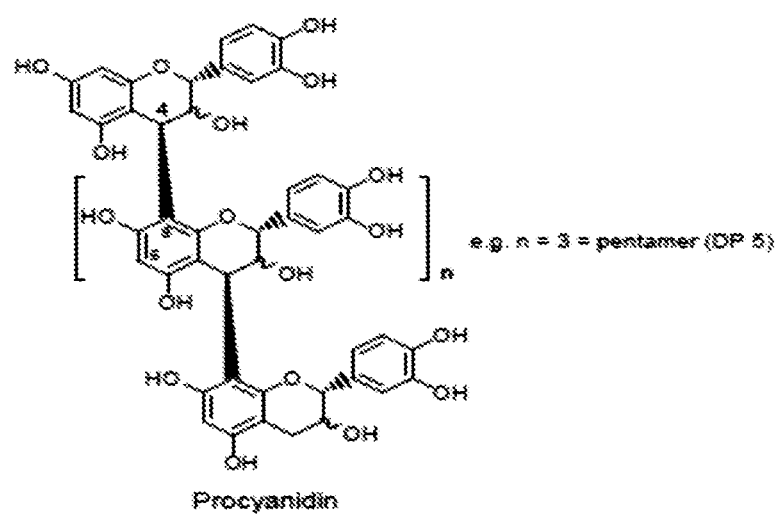

Polyphenol content was estimated with Folin-Ciocaltue method as Gallic acid equivalent (Singleton V. L and Rossi J. A. American Journal of Ecology and Viticulture, 1965, 16, pp. 144-158) and Procyanidin type B polymers was within a range of 5-20% with methylxanthines less than 0.1% (w/w). Procyanidin type A and procyanidin B type polymers are different groups of polyphenol polymers with difference in type of linkages. General chemical structure comprises linear chains of flavan-3-ols linked together through C(4)-C(8) bonds to form Type B bonds and by an ether linkage between C(2) and (C4) of the successive units and the oxygen at the C(7) position and C(6) or C(8) positions of the lower unit to form type A linkages (FIG. 1).

Cocoa beans were reported to contain type-B procyanidins and were shown to exhibit many health beneficial pharmacological effects, such as antioxidant, anti-inflammatory, immunomodulatory, gastroprotective, anti-lipidemic, anti-obesity and cognition improving properties when consume orally at significant levels.

Procyanidin content was measured on a HPLC instrument fitted with a normal phase column using mobile phase containing solvent (A) water containing 0.2% acetic acid and (B) 95% methanol containing 0.2% acetic acid under a linear gradient 0-40% B in 45 minutes. The method produced clear resolution for the peaks starting from monomer to decamer and total procyanidins were estimated by employing (−) epicatechin (Sigma Aldrich, USA; CAS #490-46-0) as analytical standard.

Detailed in vivo study has undertaken on normal and fat diet induced hyperlipidemic adult rats of Wistar strain (200-220 g body weight) to assess the effect of soluble fiber encapsulated cocoa polyphenol isolates on blood lipid profile management, and on other hematological parameters. Animal experiments were designed and conducted in strict accordance with the ethical norms approved by the Institutional Animal Ethics Committee falling in line with the CPCSEA guidelines. Animals were rendered hyperlipidemic by providing high fat diet (HFD) prepared by mixing cholesterol (1%), sodium cholate (0.5%), and rendered fat (5%) with the standard lab animal feed. The animals were closely monitored and their cholesterol level was checked at constant intervals for 3 months. The hyperlipidemic animals were randomly placed in two different groups A, and B with six animals per group. The group A was provided with the Soluble fiber encapsulated cocoa polyphenol (Extract A) containing 300 mg/g polyphenol content, 300 mg/g soluble dietary fiber and 40 mg/g theobromine at 250 mg/kg body weight; group B was maintained as a normal hyperlipidemic group without cocoa treatment and group C was the normal animals. The extracts were administered by oral gavage in the morning. Body weight of each animal on every day, and serum samples of randomly selected animals from each group at the beginning and end of the study (30th day) was checked for the serum glucose, cholesterol, triglycerides, high density lipoprotein (HDL), low density lipoprotein (LDL), and very low density lipoprotein (VLDL). All the grouped data were statistically evaluated with SPSS 11.0 software. Data collected were statistically analysed using non parametric statistical methods. A value of $p<0.05$ was considered to indicate statistical significance. All results are expressed as mean±standard deviation.

In the 30 days study, soluble fiber encapsulated cocoa polyphenol isolate (Extract A) was found to be effective in reducing the lipid profile, (total cholesterol, LDL and triglycerides) and also for enhancing HDL. Group A has produced a relative reduction of 53% in TC, 39% in TG, 64% in LDL and an increase of 1.2% in HDL as compared to the hyperlipidemic control group B which does not have any treatment. The observed reduction was statistically significant with respect to the control group B and was similar to normal animals. There was also a reduction in serum glucose level, when treated with soluble fiber encapsulated cocoa polyphenols (Extract A) (Group A) compared to the non-treated hyperlipidemic rats (FIG. 12).

The invention will now be illustrated with working examples. It is to be understood that the specific example being given here are by way of illustration and are not intended to be taken restrictively to imply any limitation on the scope of the present invention.

The present invention relates to a novel method/process for the direct extraction and fractionation of cocoa beans into various value-added products of organic quality as dietary supplements, functional food ingredients or cosmeceuticals. The process primarily includes ultrasound aided solvent extraction in a continuous mode to facilitate the commercial scale extraction of several tons of raw materials, say 10 to 50 tones, per day in a single plant. A suitable design of the ultrasound aided plant suitable for automation was provided in the present invention. The liquid extract was collected and processed to produce a variety of value added products such as cocoa polyphenols enriched with procyanidin type B oligomers, detheobrominated cocoa polyphenols and procyanidins, Theobromine enriched cocoa polyphenols, cocoa dietary fiber, cocoa soluble fiber, soluble fiber encapsulated cocoa polyphenols, cocoa proteins and their hydrolysates and finally cocoa oleoresin having the characteristic aroma and taste of chocolates.

The process comprises steps including, a. drying cocoa beans at 50 to 60° C. and coarse grinding and flaking to 1 to 5 mm pieces and extracting with a mixture of acetone/water (60 to 40 v/v) or ethanol/water (60 to 40 v/v) or water containing 0.1 to 0.5% acids such as acetic acid under ultrasound in a specially designed and developed continuous stainless steel extractor at 40 to 60° C., fitted with controlled temperature regulated automatic operation system. Filtering the miscella and evaporating under reduced pressure to contain less than 20 ppm solvent residue, shall provide a free flowing dark brown liquid called oleoresin suitable for flavor application.

b. the waste obtained after hexane/acetone extraction of oleoresin was dried under vacuum at a temperature of less than 50° C. to remove the imbibed solvent to less than 5% level without damaging the carbohydrates, fibers or proteins in cocoa matrix and converted to cocoa dietary fiber. By suitable aqueous extraction of the fiber with the help of amylases, amyloglucosidases and proteases under the influence of ultrasound can lead to the water extraction of soluble fiber along with the carbohydrates and some proteins. Concentration of the aqueous extract followed by alcohol precipitation provides soluble fiber, which can be further dissolved in water and spray dried to get soluble dietary fiber of cocoa beans.

c. The proteins can be extracted with water at pH 10 to 12 followed by acidification to pH 4 to 4.5 to precipitate the proteins. Filtration followed by dissolution of the precipitate at pH 7.0 and spray drying produces cocoa proteins, which can be further dissolved in water and perform membrane filtration to obtain high purity proteins. Further hydrolysis of proteins with proteases can produce protein hydrolysates for functional applications such as food supplements.

d. The liquid extract, called miscella can be further concentrated at controlled temperature of less than 45° C. and subject to adsorption and/or ion chromatography to isolate polyphenols and methylxanthines to prepare unique compositions of polyphenols with or without methylxanthines. Briefly, the concentrated miscella having 15 to 20% w/v total dissolved solids was concentrated and allowed to settle at low temperature, preferably below 20° C. for 3 to 5 hours and filtered. The filtrate is loaded onto an adsorbent divinyl benzene-crosslinked polystyrene resin column and washed repeatedly with water at 25° C. to 30° C. and then with hot water at 40-50° C. and further with water containing 1 to 3% ethanol. After the washings, column is eluted with ethanol alone or ethanol and water mixture, most preferably 70 to 95% ethanol v/v. The column eluent is collected, evaporated under vacuum or most preferably spray dried to get free flowing polyphenol rich powder containing procyanidin type B polymers containing monomer to decamer (>70% epicatechin equivalent, when calculated using HPLC-fluorescence method of Robbins R J et al, Journal of AOAC international, 2012, 95 (4), 1153-1160)) and not less than 10% (w/w) of theobromine as per HPLC method of quantification. Alternatively, the resin can be changed to a polyamide resin and elute the same way as before to selectively remove the methylxanthins from polyphenols to produce cocoa polyphenols (>95%) and methylxantnines less than 0.1% (w/w).

e. The liquid extract called miscella can be concentrated to remove all the organic solvents and the resulting aqueous layer can be processed by a liquid-liquid extraction process for preparing the extract containing 300 mg/g to 500 theobromine mg/g, 70 to 100 mg/g caffeine and 70 mg/g to 100 mg/g epicatechin with an overall recovery of not less than 80%. Briefly, the process include the extraction of the aqueous concentrate with ethyl acetate and further partition of the ethyl acetate layer with acidified water and concentration to either powder or liquid form.

f. Finally the soluble fiber isolated from cocoa can also be used as a microencapsulating agent either alone or in combination with other natural gums such as fenugreek galactomannans to produce encapsulated cocoa polyphenols with enhanced stability.

The extract obtained from the process is cocoa beans derived ingredients, with high antioxidant values, as evident from the high ORAC (oxygen radical absorbing capacity) value, minimum of 5000 µmol TE/g and >100 gallic acid equivalent of CAP-e values (cellular antioxidant protection values) for a soluble fiber encapsulated cocoa polyphenol with not less than 25% gallic acid equivalent polyphenol content.

The present invention also relates to a process for the preparation of highly stabilized water soluble polyphenol composition from various cocoa beans (fermented, unfermented or partially fermented) for the best bioactivity as exemplified by the hypolipidemic activity in fat diet induced hyperlipidemic rats.

The present invention also describes a process for the isolation of more than 980 mg/g gallic acid equivalent polyphenols containing not less than 700 mg/g procyanidins and its formulation to stable not less than 25% gallic acid equivalent polyphenol powder containing not less than 17% procyanidins for delivering the maximum health benefits such as in vivo antioxidant effect, Cholesterol lowering effect and overall cardiac health with a minimum of 24 months of shelf life when stored in closed containers under ambient conditions etc.

EXEMPLARY EMBODIMENTS

Embodiment A is a process for the complete fractionation of cocoa beans with 'zero waste' into various value-added ingredients comprising the steps of
a) (i) cutting, flaking and powdering the dried cocoa beans and their ultrasound aided extraction with aqueous admixture of polar organic solvents such as lower aliphatic alcohols or lower aliphatic ketones or water alone,
   (ii) filtering to separate the solvent extract and residue and
   (iii) evaporating the solvent extract under reduced pressure to obtain a concentrate rich in polyphenols, procyanidins, theobromine, and other phytochemicals present in cocoa beans.
b) (i) evaporating the concentrate mentioned under step (a) (iii) at greater than 100° C. for about 2 to about 7 hours.
   (ii) blending with emulsifiers to produce dark free flowing viscous liquid for using as flavoring ingredient
   (iii) having a composition of 10 to 20% fat, 35 to 50% carbohydrates, 15 to 25% proteins and 3 to 6% theobromine
c) (i) evaporation and concentration of the alcohol-water or ketone-water extract of cocoa mentioned in step a)
   (ii) to a dissolved solid content of about 4 to about 25%.
   (ii) chromatographically separating said concentrated extract
   (iii) eluting the column with lower alcohols and acetone either alone or in combination with water
   (iv) evaporating the eluted filtrate under vacuum to obtain a free flowing procyanidin type B polymer-rich polyphenolic extract having a composition of 950 to 990 mg polyphenols and 10 to 50 mg theobromine
d) (i) evaporation and concentration of the alcohol-water or ketone-water extract of cocoa mentioned in step a)
   (ii) to a dissolved solid content of about 4 to about 25%,
   (ii) chromatographically separating said concentrated extract
   (iii) eluting the column with lower alcohols and acetone either alone or in combination with water
   (iv) evaporating the eluted filtrate under vacuum to obtain a free flowing procyanidin type B polymer-rich polyphenolic extract having a composition of 700 to 800 mg polyphenols with not more than 10 mg/g (0.1%) theobromine as a de-theobrominated cocoa procyanidins.
e) (i) washing the chromatography column after step d) with demineralized water and collection of column wash
   (ii) concentration of the column wash
   (iii) evaporating the column wash
   (iv) extraction of the concentrated column wash with ethyl acetate.
   (v) partition of ethyl acetate layer with acidified water.
   (vi) spray drying to get a theobromine-rich powder having a composition of not less than 400 mg/g theobromine
f) (i) extracting the concentrate obtained in step a) (iii) with ethylacetate
   (ii) partitioning the ethylacetate layer with acidified water
   (iii) concentration and spray drying the acidified water layer to get an extract having a composition of 300 to 500 mg/g theobromine and 70 to 1 mg/g caffeine containing extract
(g) drying the residue left after solvent extraction in step (a) under vacuum to produce a unique composition of de-bittered dietary fiber and proteins of cocoa suitable for food applications, having a composition of 500 to 600 mg/g dietary fiber and 200 to 300 g proteins.
h) ultrasound aided enzymatic extraction of the total dietary fiber of cocoa obtained in claim 1(g) to selectively extract the soluble dietary fiber of cocoa beans with the steps comprising
   (i) Mixing the dietary fiber obtained from step 1(g) with 10 times of water
   (ii) Treatment with amylase, amyloglucosidase and proteases under optimum pH conditions
   (iii) Ultrasonication below 60° C.
   (iv) Filtration and concentration of the filtrate
   (v) Precipitation with alcohol and drying under reduced pressure to get soluble dietary fiber containing not less than 700 mg/g fiber content
i) (i) digesting the protein rich cocoa dietary fiber obtained in step 1 (g) with alkaline solution.
   (ii) centrifugation and acidification of the supernatant solution to acidic pH with dilute mineral acids to precipitate cocoa beans proteins.
   (iii) adjusting pH and membrane filtration and spray drying to get cocoa proteins containing 700 to 800 mg/g protein content.
j) treating proteins obtained under claim 1(g) with proteases enzymes under ultrasonication followed by spray drying to provide cocoa protein hydrolysates for functional applications.
i) (i) preparation of water solution of cocoa polyphenols prepared under 1(c) and soluble fiber prepared under 1(h) separately
   (ii) mixing them in the presence or absence of other soluble fibers under high pressure homogenization conditions.
   (iii) spray drying to provide unique composition of cocoa fiber encapsulated cocoa polyphenols compositions such as 400 mg/g polyphenols and 350 mg/g soluble fiber.

Embodiment B is a process of embodiment A wherein the cocoa beans are fermented, unfermented or partially fermented.

Embodiment C is a process of embodiment A wherein the cocoa beans particles produced by the step of cutting, flaking and powdering is about 0.1 to about 10 mm in size.

Embodiment D is a process of embodiment A wherein the evaporation in step a) (iii) is carried out at a temperature of about 40° C. to about 60° C.

Embodiment E is a process of embodiment A wherein the pressure in step a (iii) is about 600 mmHg to about 750 mmHg Embodiment F is a process of embodiment A wherein the supernatant solution in step (g) (ii) has a pH of about 2 to about 5.

Embodiment G is a process of embodiment A wherein the emulsifier of step b (ii) comprises sugar syrup, glycerol, propylene glycol or the like.

Embodiment H is a process of embodiment A wherein the pH of the alkaline solution of step (g) (i) is in the range of about pH 10 to about 12.

Embodiment I is a process of embodiment A wherein the mineral acid in step (g) (ii) comprises hydrochloric acid, sulphuric acid, phosphoric acid or like.

Embodiment J is a process of embodiment A wherein the protease enzyme of step (h) is selected from chymotripsyn and amyloglucans.

Embodiment K is a process of embodiment A the soluble fiber of step (h) is selected from gum *acacia*, fenugreek.

Embodiment L is a process of embodiment A wherein the cocoa fiber encapsulated cocoa polyphenols of step (h) comprises not less than 40% cocoa polyphenols and 25% dietary fiber.

Embodiment M is a process of embodiment A wherein the solvent extraction of step (a) can be carried out directly on cocoa beans that have not undergone defatting process.

Embodiment N is a process of embodiment A wherein the total polyphenol of the extract of step (c) is about 950 mg/g to about 990 mg/g gallic acid equivalent, the amount of procyanidin oligomers (monomer to decamer) range from about 400 mg/g to about 700 mg/g and the amount of methylxanthins (as theobromine and caffeine) as 10 mg/g to 50 mg/g Embodiment O is a process of embodiment A wherein the total polyphenol of the extract of step (c) is about 700 mg/g to about 800 mg/g gallic acid equivalent, the amount of procyanidin oligomers (monomer to decamer) range from about 300 mg/g to about 500 mg/g and the amount of methylxanthins (as theobromine and caffeine) is not more than about 0.1% (w/w)

Embodiment P is a process of embodiment A wherein the chromatography stationary phase of step c) (ii) is a resin comprising divinyl benzene-cross linked polystyrene or polyamide.

Embodiment Q is a process of embodiment A where in the polyphenols with greater than 950 mg/g gallic acid equivalent and containing not less than 5% (w/w) theobromine is prepared by changing the chromatographic stationary phase as selective adsorbent resins.

Embodiment R is a process of embodiment A whereby a unique composition of theobromine (not less than 400 mg/g), is obtained as free flowing water dispersible powder.

Embodiment S is a process of embodiment A whereby a unique composition of cocoa beans derived methylxanthins having a content of about 300 mg/g to about 50 mg/g of theobromine and about 70 mg/g to about 100 mg/g of caffeine was obtained Embodiment T is a process of embodiment A wherein the residue after solvent extraction is dried under vacuum at a temperature of about 50 to about 70° C. and powdered to provide a unique composition of tasteless cocoa dietary fiber with mild characteristic smell of chocolate, containing not less than 55% total dietary fiber, not less than 20% proteins, and not less than 15% carbohydrates.

Embodiment U is a process of embodiment A wherein the residue of dietary fiber obtained is further extracted with water under ultrasound conditions at less than about 4 to about 6 hours and the water extract was concentrated and mixed with alcohol to precipitate the soluble fiber having not less than about 40 to about 70% fiber content.

Embodiment V is a process of embodiment A wherein the residue of dietary fiber obtained is extracted with dilute alkali to obtain water soluble powder containing not less than about 60% (w/w) to about 80% (w/w) cocoa bean proteins and is further treated with proteases to provide cocoa bean protein hydrolysates.

Embodiment W is a process of embodiment A wherein the crude extract of cocoa beans is roasted with sugar syrup at about 100° C. to 120° C. for about 4 to 6 hours to produce a unique chocolate flavor, having a composition of cocoa fat of about 10 to about 20%, carbohydrates of about 35 to about 50% proteins of about 15 to about 25% and theobromine of about 3 to about 6%

Embodiment X is a composition comprising cocoa polyphenols/procyanidins and soluble dietary fiber containing not less than about 25% to about 40% polyphenols and about 25% to about 40% soluble dietary fiber.

Embodiment Y is a stable composition of polyphenols/procyanidins of cocoa obtained by the microencapsulation using soluble dietary fiber-derived from cocoa beans.

Embodiment Z is a water dispersible and sustained release formulation of cocoa polyphenols with cocoa soluble dietary fiber capable of forming a colloidal dispersion of bioactive cocoa polyphenols in gastric fluid.

Embodiment AA is a stable composition of cocoa antioxidants having a minimum of about 12 months shelf life for blood lipid profile management comprising cocoa polyphenols having not less than about 250 mg/g polyphenols and about 300 mg/g soluble dietary fiber.

Embodiment AB is a method for reducing blood cholesterol levels and body weight controlling in mammals comprising the steps of administering an effective amount of cocoa procyanidine of type B polymers encapsulated in cocoa dietary fiber.

Embodiment AC is a unique composition of cocoa polyphenols/procyanidins with cocoa soluble dietary fiber for cosmetic applications.

Embodiment AD is a unique process for producing antioxidant dietary fiber from cocoa beans for functional food applications Embodiment AE is a unique composition of dietary fiber and protein rich fraction of cocoa beans with mild characteristic aroma of chocolate for fiber/protein fortification in cocoa based food items.

EXAMPLES

Example 1

Ultrasound Aided Continuous Extraction Using Acetone/Water

100 Kg of dried fermented cocoa beans (polyphenol content 2.8% gallic acid; theobromine content 0.7%; caffeine 0.2%) were crushed and flaked into a particle size of less than 5 mm, and slowly charged into an ultrasound-assisted continuous extractor having a length of 6 meters and 0.4 meter width for a height of 0.3 meter, developed as shown in FIG. 2.

A mixture of acetone and water, containing 70% (v/v) of acetone, was slowly sprayed into ultrasound extraction vessel to completely immerse the cocoa particles in the solvent.

Ultrasound was produced from an ultrasound generator (Hielscher, Germany) fitted to the body of the extractor in series.

The bed carrying cocoa powder was moved at a speed of . . . 1 m/hr over the length of 6 meter in such a way that the extraction completes when the raw material reach from one end to the other.

The duration of ultrasound was automatically controlled by a PLC system connected with a digital temperature probe, in such a way that the ultrasound cuts off when temperature exceeds 60° C.

Ultrasound was applied as pulse of duration 1 to 5 min.

The extract containing micelle was drained off automatically at regular intervals (2 h) through definite outlets along the continuous extractor and stored in a separate tank.

The extraction was continued up to 6 to 12 h.

Combine the whole extracted micelle and was evaporated under reduced pressure to get 55 L of free flowing dark brown cocoa flavour liquid with 10.5 kg dry extract.

Results: The extract was found to contain phytochemicals of cocoa such as polyphenols, methylxanthines, cocoa fat, phenylethylamine and flavouring substances with a polyphenol content of 25.7% gallic acid equivalent, theobromine 6.4% content and caffeine 2.1%, on the basis of dry extract. Recovery of polyphenol was found to be 96.4% of the polyphenols in raw cocoa beans.

The above extraction procedure was repeated with unfermented cocoa beans having a polyphenol content of 6.1% GAE; theobromine 1.2%; caffeine 0.35%.

Result: This process obtained the yield of 12.3 kg dry extract which was found to contain 48.50% GAE polyphenols, 5.3% theobromine and 2.2% caffeine with an overall extraction recovery of 97.7%.

The residue after extraction was treated in de-solventisation tank working at a temperature of 60 to 80° C. under vacuum to remove the imbibed solvent to less than 0.5% level.

It was further dried in a rotory vacuum paddle drier.

Result: The dry extract obtained is solvent free (<50 ppm) cocoa residue (82.0 Kg from fermented cocoa and 79.5 Kg from unfermented cocoa).

Example 2

Ultrasound Aided Continuous Extraction Using Ethanol/Water

100 Kg of dried fermented cocoa beans (polyphenol content 2.8% gallic acid; theobromine content 0.7%; caffeine 0.2%) were crushed and flaked into a particle size of less than 0.5 mm, and slowly charged into an ultrasound-assisted continuous extractor, developed as shown in FIG. 1.

A mixture of ethanol and water, containing 70% (v/v) of ethanol, was slowly sprayed into ultrasound extraction vessel to completely immerse the cocoa particles in the solvent. Ultrasound was produced from an ultrasound generator (Hielscher, Germany) fitted to the body of the extractor in series.

The bed carrying cocoa powder was moved at a speed of 1.0 m/hr over the length of . . . 6 meters in such a way that the extraction completes when the raw material reach from one end to the other.

The duration of ultrasound was automatically controlled by a PLC system connected with a digital temperature probe, in such a way that the ultrasound cuts off when temperature exceeds 60° C.

Ultrasound was applied as pulse of duration 1 to 5 min.

The extract containing micelle was drained off automatically at regular intervals (2 h) through definite outlets along the continuous extractor and stored in a separate tank.

The extraction was continued up to 6 to 12 h.

The whole extracted micelle was combined and was evaporated under reduced pressure.

Result: The process yield 53.0 L of free flowing dark brown cocoa flavour liquid with 10.4 kg dry extract. The extract was found to contain phytochemicals of cocoa such as polyphenols, methylxanthines, cocoa fat, phenylethylamine and flavouring substances with a polyphenol content of 25.96% gallic acid equivalent, theobromine 6.53% content and caffeine 1.9%, on the basis of dry extract. Recovery of polyphenol was found to be 96.4% of the polyphenols in raw cocoa beans.

The above extraction procedure was repeated with unfermented cocoa beans having a polyphenol content of 6.1% theobromine 1.2%; caffeine 0.35%.

Result: The process obtained the yield of 13.1 kg dry extract which was found to contain 44.85% polyphenols, 5.5%, theobromine and 2.3% caffeine with an overall recovery of 96.3%.

The residue after extraction was treated in de-solventisation tank working at a temperature of 60 to 80° C. under vacuum to remove the imbibed solvent to less than 0.5% level. It was further dried in a rotory vacuum paddle drier.

Result: A solvent free (<50 ppm) cocoa residue (61.5 Kg from fermented cocoa and 58.5 Kg from unfermented cocoa) was obtained.

Example 3

Ultrasound Aided Continuous Extraction Using Water

100 Kg of dried fermented cocoa beans (polyphenol content 2.8% gallic acid; theobromine content 0.7%; caffeine 0.2%) were crushed and flaked into a particle size of less than 0.5 mm.

It is then slowly charged into an ultrasound-assisted continuous extractor developed as shown in FIG. 1.

Water was slowly sprayed into ultrasound extraction vessel to completely immerse the cocoa particles in the solvent. Ultrasound was produced from an ultrasound generator (Hielscher, Germany) fitted to the body of the extractor in series.

The bed carrying cocoa powder was moved at a speed of . . . 1.0 . . . m/hr over the length of . . . 6 meters in such a way that the extraction completes when the raw material reach from one end to the other.

The duration of ultrasound was automatically controlled by a PLC system connected with a digital temperature probe, in such a way that the ultrasound cuts off when temperature exceeds 60° C.

Ultrasound was applied as pulse of duration 1 to 5 min.

The extract containing micelle was drained off automatically at regular intervals (2 h) through definite outlets along the continuous extractor and stored in a separate tank.

The extraction was continued up to 6 to 12 h.

Combined the whole extracted micelle and evaporated under reduced pressure.

Result: 275 L of free flowing dark brown cocoa flavour liquid with 25.2 kg dry extract was obtained. The extract was found to contain phytochemicals of cocoa such as polyphenols, methylxanthines, cocoa fat, phenylethylamine and flavouring substances with a polyphenol content of 9.2% gallic acid equivalent, theobromine 2.75% content and caffeine 0.7%, on the basis of dry extract. Recovery of polyphenol was found to be 82.1% of the polyphenols in raw cocoa beans.

The above extraction procedure was repeated with unfermented cocoa beans having a polyphenol content of 6.1% theobromine 1.2%; caffeine 0.35%.

Result: A yield of 23 Kg dry extract could be observed which was found to contain 21% polyphenols, 6.5% theobromine and 1.3% caffeine.

The residue after extraction was treated in de-solventisation tank working at a temperature of 60 to 80° C. under vacuum to remove the imbibed solvent to less than 0.5% level. It was further dried in a rotory vacuum paddle drier.

Result: A solvent free (<50 ppm) cocoa residue (168 Kg from fermented cocoa and 155 Kg from unfermented cocoa) could be obtained.

Example 4

Purification of Polyphenols

The aqueous extract obtained from fermented cocoa, after removal of the solvent (acetone: <1%) were filtered under vacuum and subjected to a purification processes using adsorption resin. A macroporous resin divinylbenzene-crosslinked polystyrene resin, (AMBERLITE) (M/s Rohm and Haas. France) used for purification of this processes. The steps to be followed for purifying polyphenol in a column are:

Packing the column: 100 L of resin was filled uniformly into a column with an internal diameter of 12 inch without trapping any air pockets to a height of 8 feet (Bed volume BV=170 L per column) to obtain a uniform bed.

Washing the column with distilled water. The resin is washed with 200 L of demineralized water with a flow rate of 55 L/h About 100 L of Polyphenol containing cocoa extract (obtained from Examples 1, 2 & 3) having a total dissolved solid level of 20.5% (w/v) having a polyphenol content of 25% gallic acid equivalent was loaded to the column filled with the adsorption resin, and allow the polyphenols to get adsorbed into the resin. The aqueous extract was passed through column filled with 100 L of adsorbent resin at a flow of 20 L/h.

The column was washed with 300 L of demineralized water (three column volume of cold water) followed by two column volume of hot water (60 to 65° C.) with a flow of 100 L/hr to eliminate the more polar compounds which are not polyphenols and are retained on the column.

Then further the column washed with 200 L of hot water (60° C.) to eliminate any other impurities remains in the column. The polyphenols retained on the column will be then desorb.

The polyphenols were eluted with 125 L of 90% aqueous ethanol with a flow rate of 20 L/h. The compound of interest retained in the column are eluted.

Washing the column with water.

The purified fraction was distilled and the aqueous extracts were spray dried to obtain a polyphenol-rich free flowing powder.

The purified extract fraction obtained is denominated as 'Eluent (A)'.

The column was washed with 100 L of demineralized water with a flow rate of 20 L/hr.

The first aqueous 25 L obtained are called 'Eluent (B)'.

The purified extract fractions 'Eluent (A)' and 'Eluent (B)' from the aqueous extract portions, were pooled together (150 L) and concentrated in an evaporator system at 60° C. and 650 mmHg.

Results: 5.03 Kg of a viscous 20° Brix concentrate was obtained, with polyphenol content of 953 mg/g and theobromine 47 mg/g with an overall polyphenol recovery of 98%.

The above procedure was repeated with unfermented cocoa extract obtained from acetone water extracts.

Results: About 9.7 Kg polyphenol extract with 948 mg/g gallic acid equivalent and theobromine 51 mg/g with an overall polyphenol recovery of 98.3%.

The polyphenolic extract with more than 40 mg/g theobromine obtained in the above process can be further subjected to an ion exchange chromatographic separation to completely remove theobromine and caffeine to produce more than 990 mg/g polyphenolic extract.

The above procedure of purification can be performed on acetone/water or ethanol/water or aqueous extract of fermented or unfermented or partially fermented cocoa beans to produce the polyphenol rich concentrate containing >98% polyphenol content with >95% recovery. The method has the advantage of quantitative recovery in the isolation process with no separate defatting steps such as hexane extraction or super critical extraction to remove the cocoa fats.

Example 5

Selective Removal of Methylxanthines (Caffeine and Theobromine) from Cocoa Polyphenols The aqueous extract obtained from fermented cocoa, after removal of the solvent (acetone: <1%) were filtered under vacuum and subjected to a purification processes using a cation exchange resin. A macroporous resin divinylbenzene-crosslinked polystyrene resin, (Thermax-414) (M/s Thermax, India) used for purification of this processes. The steps to be followed for purifying polyphenol in a column are:

The column with an internal diameter of 12 inch was packed with 100 L of Thermax resin, to a height of 8 feet (Bed volume BV=170 L per column) uniformly without trapping any air pockets, to obtain a uniform bed. The column is packed following the manufacturer's instructions consisting of introducing the resin inside the column preventing the formation of air pockets between its particles to thus obtain a uniform bed.

The resin is washed with 200 L of demineralized water with a flow rate of 55 L/h Polyphenol containing cocoa extract obtained from example 1 (100 L), having a total dissolved solid level of 20.1% (w/v) was adjusted to pH 3.5 to 4.0 with acetic acid loaded to the column filled with the cation exchange resin, and allow the methylxanthines to get adsorbed into the resin.

The polyphenol rich fraction was collected, concentrated under vacuum to get 9.58 kg of powder with 730 mg/g polyphenol and 7 mg/g theobromine and 2 mg/g caffeine with an overall polyphenol recovery of 96.3%.

The binded methylxanthines further washed with five column volume of distilled water Eluting the methylxanthine rich portion with 100 L of aqueous ethanol containing 3% ammonia solution and evaporated to remove ammonia. Finally an extract containing 345 mg/g theobromine and 70 mg/g caffeine was obtained.

Results: 9.58 Kg of detheobrominated cocoa polyphenol extract containing 730 mg/g polyphenols with less than 0.1% methylxanthines was obtained with an overall polyphenol recovery of 96.3%. In addition, 2.05 kg extract containing 345 mg/g theobromine and 70 mg/g caffeine was also obtained with a theobromine recovery of 68.9%.

Example 6

Preparation of Methylxanthines—Rich Cocoa Polyphenols

100 L of aqueous extract obtained from fermented cocoa (Example 1), after removal of solvent (acetone) was extracted with 100 L of ethyl acetate (1:1, v/v) by a liquid-liquid extractor.

The extraction procedure was repeated 3 times.

The obtained ethyl acetate fractions were pooled (278 L). This was concentrated up to one by third (92 L).

It was further separated with 90 L, 1 N HC (1:1, v/v) and separation procedure repeated 3 times.

The acid portions are further concentrated to reduce under vacuum via low temperature evaporation system to a brix level of 20°, Results: 3.2 kg with 313 mg/g theobromine and 114 mg/g caffeine was obtained with a recovery of 82% recovery.

The above methylxanthine rich micelle obtained from examples 5 & 6 combined with cocoa extract micelle obtained from examples 1, 2, 3 & 4 to get cocoa polyphenols containing maximum methyl xanthines or theobromine. For example 1.25 L methylxanthine rich portion of example 6 can be mixed with 1.0 L extract from example 4 and spray dried to get a product containing 400 mg/g cocoa polyphenols and 200 mg/g theobromine and 76 mg/g caffeine.

Example 7

Isolation of Cocoa Dietary Fiber (Ultrasound-Assisted Enzymatic Method)

80 Kg cocoa residue (spent of cocoa) obtained from example 1 was treated 1000 L water adjusted to pH 6.0.

To this alpha-amylase was added at 500 ppm concentration and heated to a temperature of 90-95° C. for 15 min.

It was cooled to room temperature and the pH was adjusted to 7.5 with 0.5% sodium hydroxide solution.

To this solution, 100 ppm protease solution was added and kept 30 minutes at 60° C.

The solution is cooled to room temperature and adjust pH to 4-4.5 by adding 0.3% HCl.

500 ppm of amyloglucosidase was added to this and kept 30 minutes.

The whole residue was filtered by vacuum and residue dried at RVPD.

Results: Obtained 65 kg insoluble fiber (84% dietary fiber) and the filtrate was concentrated and precipitated with 90% aqueous alcohol to obtained 5 kg soluble fiber (72.3% fiber content).

Example 8

Extraction of Cocoa Proteins 100 kg cocoa residue (spent of cocoa) was charged to an ultrasound sonication extractor.

1000 L was added and adjusted at pH to 11-12 with potassium hydroxide. Ultrasound was applied as before The duration of ultrasound was automatically controlled by a PLC system connected with a digital temperature probe, in such a way that the ultrasound cuts off when temperature exceeds 60 C.

Ultrasound was applied as pulse of duration 1 to 5 minutes.

The extract containing micelle is filtered and stored in a separate tank with regular intervals of time (2 h).

The extraction was continued up to 8 h and filtered.

pH of the filtrate was adjusted to 4.5 by adding 1 N HCl.

The precipitated proteins were again dissolved at pH 7.0.

It was freeze dried or spray dried to get powder containing not less than 35% protein content Alternatively, the alkaline extract containing proteins can be adjusted to pH 7.0 and can be concentrated using membrane filtration using the 5 KD molecular weight cut off membranes to remove all the polysaccharides, fats, and small molecule impurities and protein-rich extract can be concentrated. Protein content: 74.8%.

Example 9

Microencapsulation of Cocoa Polyphenols with Cocoa Soluble Fiber

Soluble fiber obtained from example 7 was employed as a matrix for the microencapsulation of cocoa polyphenols to produce stable, water soluble spherical beads of cocoa polyphenols of around 1.2±0.2 μn particles. Soluble fiber isolated from cocoa beans swelled in water to form a gummy solution capable of forming films on evaporation;

500 g of cocoa polyphenols prepared in example 4 having a polyphenol content of 92% was dissolved in water at 15 to 20% brix level and filtered to get a clear solution.

500 g of soluble fiber prepared under example 7, having a fiber content of 73% was dissolved at 20% brix level and sonicated for 20 min to get a free flowing solution.

The polyphenol solution was slowly mixed with the soluble fiber solution under homogenization.

The mixture of solution was again subjected to ultrasonication as pulses of 1 to 3 min for 30 min at a temperature not more than 45° C.

The solution was checked for particle size.

Uniform solution thus obtained with particles of 1±0.2 μM.

This was spray dried to get free flowing powder of soluble fiber encapsulated cocoa polyphenols with 46% polyphenols and 35% fiber content.

Coco polyphenols or cocoa methylxanthines prepared in examples 4, 5, or 6 can also be used for encapsulation. Other soluble dietary fibers having encapsulating properties, like fenugreek galactomannans, gum *acacia*, non-digestible starches, etc, can also be used, either alone or in combination with cocoa soluble dietary fiber to produce fiber encapsulated cocoa polyphenols.

Example 10

Preparation of Cocoa Extract as Flavour

The extract obtained from fermented cocoa beans as mentioned in example 1 was evaporated under reduced pressure to remove the organic solvent acetone to less than 2% level.

This is blended with 10 to 20% w/w of sugar solution and 5 to 10% of propyleneglycol.

The solution was further evaporated at 80 to 100° C. and finally heat at 100 to 120° C. for 6 h to less than 20 ppm solvent residues.

The free flowing viscous liquid was analysed collected and stored under nitrogen atmosphere for minimum 30 days to get the characteristic chocolate flavor suitable for food flavor applications.

Example 11

Estimation of Polyphenol Content

Polyphenol content was estimated with Folin-Ciocaltue method as Gallic acid equivalent (Singleton V. L and Rossi J. A. American Journal of Ecology and Viticulture, 1965, 16, pp. 144-158).

Example 12

Estimation of Procyanidins

Procyanidin content was measured as per Robbins R J et al, Journal of AOAC international, 2012, 95 (4). 1153-1160); using a HPLC instrument fitted with a normal phase column using mobile phase containing solvent (A) water containing 0.2% acetic acid and (B) 95% methanol containing 0.2% acetic acid under a linear gradient 0-40% B in 45 minutes. The method produced clear resolution for the peaks starting from monomer to decamer and total procyanidins were estimated by employing (−) epicatechin (Sigma Aldrich. USA; CAS #490-46-0 . . . ) as analytical standard.

Example 13

Estimation of Theobromine and caffeine content in cocoa beans and cocoa extracts was estimated by an HPLC procedure, based on Hung-Ju Chen et al, International Journal of Molecular Science, 2012, 260-285.

Example 14

Pharmacological Studies

Detailed in vivo study has undertaken on normal and fat diet induced hyperlipidemic adult rats of Wister strain (200-220 g body weight) to assess the effect of soluble fiber encapsulated cocoa polyphenol isolates on blood lipid profile management, and on other hematological parameters. Animal experiments were designed and conducted in strict accordance with the ethical norms approved by the Institutional Animal Ethics Committee falling in line with the CPCSEA guidelines.

Animals were rendered hyperlipidemic by providing high fat diet (HFD) prepared by mixing cholesterol (1%), sodium cholate (0.5%), and rendered fat (5%) with the standard lab animal feed.

The animals were closely monitored and their cholesterol level was checked at constant intervals for 3 months.

The hyperlipidemic animals were randomly placed in two groups (Group A and Group B) with six animals per group The group A was provided with the Soluble fiber encapsulated cocoa polyphenol (Extract A) containing 300 mg/g polyphenol content, 300 mg/g soluble dietary fiber and 40 mg/g theobromine at 250 mg/kg body weight.

The group B was maintained as a normal hyperlipidemic group without cocoa treatment and group C was the normal animals.

The extracts were administered by oral gavage in the morning.

Body weight of each animal on every day, and serum samples of randomly selected animals from each group at the beginning and end of the study (30th day) was checked for the serum glucose, cholesterol, triglycerides, high density lipoprotein (HDL), low density lipoprotein (LDL) and very low density lipoprotein (VLDL).

All the grouped data were statistically evaluated with SPSS 11.0 software.

Data collected were statistically analysed using non parametric statistical methods.

A value of $p<0.05$ was considered to indicate statistical significance. All results are expressed as mean±standard deviation.

Results: In the 30 days study, soluble fiber encapsulated cocoa polyphenol isolate (Extract A) was found to be effective in reducing the lipid profile, (total cholesterol, LDL and triglycerides) and also for enhancing HDL. Group A has produced a relative reduction of 53% in TC, 39% in TG, 64% in LDL and an increase of 1.2% in HDL as compared to the hyperlipidemic control group B which does not have any treatment. The observed reduction was statistically significant with respect to the control group B and was similar to normal animals. There was also a reduction in serum glucose level, when treated with soluble fiber encapsulated cocoa polyphenols (Extract A) (Group A) compared to the non-treated hyperlipidemic rats (FIG. 12).

Example 15

Application of 'Cocoa Flavor' Produced in this Invention as a Food Ingredient i) Chocolate:

| Ingredients | % Concentration |
|---|---|
| Cocoa Flavor | 6% |
| Cocoa powder | 8% |
| Cocoa butter | 10% |
| Milk powder | 15% |
| Sugar | 60% |
| Vanilla essence | 1% |

Cocoa butter and milk powder were combined and mixed using a blender until homogeneous. The resulting butter/milk mixture was added to the granulated sugar and mixed at 35° C. to about 90° C. until homogeneous. The remaining ingredients including cocoa powder were added and mixed until homogeneous. The homogeneous mixture was casted and cooled for half an hour to get chocolate slabs ii) Chocolate Cake:

| Ingredients | % Concentration |
|---|---|
| Butter | 20% |
| Eggs | 20% |
| Sugar | 13.7% |
| Wheat Flour | 13.2% |
| Cocoa flavor | 13.2% |
| Milk | 20% |
| Baking powder | 0.7% |

All the above ingredients except flour and baking powder as listed below were blended thoroughly. The flour and baking powder were mixed separately and mixed to the first blend to form a homogeneous paste. The blend was then applied to the butter applied pan, bake at 175° C. for 20 minutes to get brown coloured cake.

iii) Powdered Drinks Sachet:

Below mixture of ingredients was prepared as a free flowing fine powder and 5 g of the mixture was dissolved in hot water or milk at 50 to 60° C. to get a ready to drink beverage.

| Ingredients | % Concentration |
|---|---|
| Cocoa fiber | 4% |
| Cocoa powder | 4% |
| Cocoa flavor | 30% |
| Sugar | 60% |
| Vanilla | 2% |

Example 16

Application of 'Cocoa Flavonoids' Produced in this Invention as a Food Ingredient i) Chocolate:

| Ingredients | % Concentration |
|---|---|
| Cocoa powder | 8% |
| Cocoa flavonoids, (with 700 mg/g) | 0.5% |
| Cocoa butter | 16% |
| Sugar | 60% |
| Milk powder | 15% |
| Vanilla | 0.5% |

Cocoa butter and milk powder were combined and mixed using a blender until homogeneous. The resulting butter/milk mixture was added to the granulated sugar and mixed at 35° C. to about 90° C. until homogeneous. The remaining ingredients including cocoa powder were added and mixed until homogeneous. The homogeneous mixture was casted and cooled for half an hour to get chocolate slabs.

ii) Chocolate Shake:

| Ingredients | % Concentration |
|---|---|
| Cocoa powder | 32% |
| Cocoa flavonois | 4% |
| Milk powder | 14% |
| Sugar | 50% |

12.5 g of the above mix was added in 500 ml milk and blended thoroughly in a blender.

iii) Powdered Drink Sachet:

| Ingredients | % Concentration |
|---|---|
| Cocoa powder | 20% |
| Cocoa flavonoids | 4% |
| Sugar | 72% |
| Vanilla | 4% |

Above mixture of ingredients was prepared as a free flowing fine powder and 5 g of the mixture was dissolved in hot water or milk at 50 to 60° C. to get a ready to drink beverage.

Example 17

Application of 'Cocoa Dietary Fiber' Produced in this Invention as a Food Ingredient i) Chocolate:

| Ingredients | % Concentration |
|---|---|
| Cocoa powder | 8% |
| Cocoa butter | 15% |
| Cocoa fiber | 6% |
| Milk powder | 15% |
| Sugar | 55% |
| Vanilla | 1% |

Cocoa butter and milk powder were combined and mixed using a blender until homogeneous. The resulting butter/milk mixture was added to the granulated sugar and mixed at 35° C. to about 90° C. until homogeneous. The remaining ingredients including cocoa powder were added and mixed until homogeneous. The homogeneous mixture was casted and cooled for half an hour to get chocolate slabs.

ii) Chocolate Shake:

| Ingredients | % Concentration |
|---|---|
| Cocoa fiber | 16% |
| Milk powder | 20% |
| Cocoa powder | 14% |
| Sugar | 50% |

12.5 g of the above mix was added in 500 ml milk and blended thoroughly in a blender.

iii) Powdered Drink Sachet:

| Ingredients | % Concentration |
|---|---|
| Cocoa fiber | 16% |
| Cocoa powder | 20% |
| Sugar | 60% |
| Vanilla | 4% |

Above mixture of ingredients was prepared as a free flowing fine powder and 5 g of the mixture was dissolved in hot water or milk at 50 to 60° C. to get a ready to drink beverage.

Example 18

Application of 'Cocoa Water Extract' Produced in this Invention as a Food Ingredient i) Chocolate Jam:

| Ingredients | % Concentration |
| --- | --- |
| Fruit juice (any citrus fruit) | 60% |
| Sugar | 30% |
| Cocoa water extract | 9% |
| Pectin | 1% |

Juice and sugar were mixed in a large saucepan and place it in low flame until sugar dissolves completely. The remaining ingredient like pectin were added and mixed until it reaches the accurate consistency.

ii) Chocolate Syrup:

| Ingredients | % Concentration |
| --- | --- |
| Water | 49% |
| Sugar | 39.2% |
| Cocoa water extract | 10.8% |
| Vanilla | 1% |

Dissolve the sugar in hot water with constant stirring. When the sugar completely dissolved add cocoa water extract and vanilla essence. Stir continuously until it reaches the accurate consistency.

Example 19

Application of 'Cocoa Soluble Fiber Encapsulated Cocoa Polyphenols' Produced in this Invention as a Food Ingredient 25% cocoa polyphenols encapsulated in 30% soluble fiber was used as the ingredient i) Chocolate:

| Ingredients | % Concentration |
| --- | --- |
| Cocoa powder | 10% |
| Cocoa fiber and polyphenol mix | 6% |
| Cocoa butter | 10% |
| Milk powder | 15% |
| Lecithin | 3% |
| Sugar | 55% |
| Vanilla | 1% |

Cocoa butter and milk powder were combined and mixed using a blender until homogeneous. The resulting butter/milk mixture was added to the granulated sugar and mixed at 35° C. to about 90° C. until homogeneous. The remaining ingredients including cocoa powder were added and mixed until homogeneous. The homogeneous mixture was casted and cooled for half an hour to get chocolate slabs.

ii) Protein Bar:

| Ingredients | % Concentration |
| --- | --- |
| Cocoa fiber/polyphenol mix | 9% |
| Cocoa powder | 8% |
| Vegetable oil | 35% |
| Sugar | 30% |
| Chocolate chips | 15% |
| Baking powder | 2% |
| Vanilla | 1% |

Preheat the oven to 35° F. Mix all ingredients except the chips in a high-quality food processor, and blend until completely smooth. Stir with chocolate chips. Then pour it into a greased 8×8 square pan. Cook the chocolate protein bars for 16 minutes. Cool, then pat down with a pancake spatula. Refrigerate overnight.

iii) Chocolate Bread Spread:

| Ingredients | % Concentration |
| --- | --- |
| Cocoa powder | 16.6% |
| Cocoa fiber and polyphenol mix | 10% |
| Nuts | 13.3% |
| Vegetable oil | 10% |
| Milk chocolate chips | 16.7% |
| Sugar | 26.6% |
| Vanilla | 6.7% |

Pulverize the nuts until they form a uniform powder. Add it into the bowl containing oil and sugar, cocoa powder and vanilla. Add salt to taste. Pulverize all of the ingredients together until smooth. Pour the melted chocolate into the smooth mixture. Pulverize until well combined. Strain well. Store in the refrigerator.

Example 20

Application of 'Cocoa Theobromine' Produced in this Invention as a Food Ingredient i) Chocolate:

| Ingredients | % Concentration |
| --- | --- |
| Cocoa powder | 10% |
| Cocoa batter | 10% |
| Cocoa theobromine-20% | 0.35% |
| Milk powder | 15% |
| Lecithin | 3% |
| Sugar | 60% |
| Vanilla | 1.65% |

Cocoa butter and milk powder were combined and mixed using a blender until homogeneous. The resulting butter/milk mixture was added to the granulated sugar and mixed at 35° C. to about 90° C. until homogeneous. The remaining ingredients including cocoa powder were added and mixed until homogeneous. The homogeneous mixture was casted and cooled for half an hour to get chocolate slabs.

ii) Hot Chocolate Drink:

| Ingredients | % Concentration |
| --- | --- |
| Cocoa powder | 18% |
| Cocoa theobromine-25% | 0.66% |

| Ingredients | % Concentration |
| --- | --- |
| Milk powder | 30% |
| Sugar | 50% |
| Vanilla | 1.34% |

10 g of the above mix was added in 300 ml milk and blended thoroughly in a blender.

Example 21

Formulation of Cosmetic Ingredients with Cocoa Extracts Produced in this Invention Cocoa and its extracts were reported to have a number of benefits such as antioxidant properties, wrinkle reduction, skin softening, skin nourishment, skin hydration, and collagen maintenance. It also fight against sun damage and a good moisturizer.

(i) Face Pack
Cocoa Mask:

| Ingredients | % Concentration |
| --- | --- |
| Cocoa water extract | 25% |
| Cocoa fibre and polyphenol mix | 12.5% |
| Cocoa OR | 12.5% |
| Honey | 25% |
| Heavy cream | 12.5% |
| Oatmeal powder | 12.5% |

Mix all the ingredients to make a smooth paste, and apply it on the face. The fiber helps to form a thin layer of coating over the skin which can be peeled off and further rinsed with Water.

We claim:

1. A method for fractionation of cocoa beans into various value-added ingredients, the method comprising the steps of:
   a) (i) processing cocoa beans by cutting, flaking and powdering dried cocoa beans, and performing ultrasound aided extraction of the processed cocoa beans using an aqueous admixture of polar organic solvents to obtain a solvent extract and a cocoa residue from the processed cocoa beans,
      (ii) filtering to separate the solvent extract from the cocoa residue, and
      (iii) evaporating a first portion of the solvent extract under reduced pressure to obtain a concentrate, the concentrate being rich in polyphenols, procyanidins, and theobromine;
   b) (i) evaporating the concentrate obtained in step (a) (iii) at greater than 100° C. for a duration of time in a range from approximately 2 hours to approximately 7 hours,
      (ii) blending the evaporated concentrate with emulsifiers to produce a dark free flowing viscous liquid for using as a flavoring ingredient, the dark free flowing viscous liquid having a composition of 10% to 20% fat, 35% to 50% carbohydrates, 15% to 25% proteins and 3% to 6% theobromine;
   c) (i) evaporating and concentrating a second portion of the solvent extract obtained in step a) (ii) to a dissolved solid content in a range from approximately 4% to approximately 25%,
      (ii) column chromatographically separating the concentrated extract obtained in step c) (i)
      (iii) eluting the chromatography column of step c) (ii) with alcohols and acetone either alone or in combination with water to produce an eluted filtrate, and
      (iv) evaporating the eluted filtrate produced in step c) (iii), under vacuum, to obtain a free flowing procyanidin type B polymer-rich polyphenolic extract having a composition of 950 to 990 mg polyphenols and 10 to 50 mg theobromine per 1000 mg of extract,
   d) (i) evaporating and concentrating a third portion of the solvent extract obtained in step a) (ii) to a dissolved solid content in a range from approximately 4% to approximately 25%,
      (ii) column chromatographically separating the concentrated extract obtained in step d) (i),
      (iii) eluting the chromatography column of step d) (ii) with alcohols and acetone either alone or in combination with water to produce an eluted filtrate, and
      (iv) evaporating the eluted filtrate produced in step d) (iii), under vacuum, to obtain a free flowing procyanidin type B polymer-rich polyphenolic extract having a composition of 700 to 800 mg polyphenols with not more than 10 mg theobromine per 1000 mg of extract;
   e) (i) washing the chromatography column after step d) with demineralized water and collecting the column wash,
      (ii) evaporating and concentrating the column wash,
      (iii) extracting the evaporated and concentrated column wash with a layer of ethyl acetate, and
      (iv) partitioning the ethyl acetate layer with acidified water to produce a theobromine-rich powder having a composition of not less than 400 mg theobromine per 1000 mg of powder,
      (v) spray drying the theobromine-rich powder produced in step e) (iv);
   f) (i) extracting the concentrate obtained in step a) (iii) with a layer of ethyl acetate,
      (ii) partitioning the ethyl acetate layer with acidified water, and
      (iii) concentrating and spray drying the acidified water layer to obtain an extract having a composition of 300 to 500 mg theobromine per 1000 mg of extract, 70 to 100 mg caffeine per 1000 mg of extract, and 70 to 100 mg epicatechin per 1000 mg of extract,
   (g) drying, under vacuum, the cocoa residue left after performing the solvent extraction in step a) (i) to produce a cocoa composition of dietary fiber and cocoa proteins,
   h) performing ultrasound aided enzymatic extraction of the dietary fiber of the cocoa composition produced in step (g) to selectively extract soluble dietary fiber of the cocoa beans by performing the following steps:
      (i) mixing the dietary fiber produced in step (g) with water to form a mixture of dietary fiber and water,
      (ii) treating the mixture formed in step h) (i) with amylase, amyloglucosidase and proteases under ultrasonication at a temperature below 60° C., and
      (iii) precipitating the treated mixture of step h) (ii) with alcohol and drying the precipitated mixture under reduced pressure to obtain soluble dietary fiber and a supernatant solution;
   i) (i) digesting the cocoa composition produced in step (g) with alkaline solution, (ii) performing centrifugation and acidification of the supernatant solution to acidic pH levels with dilute mineral acids to precipitate cocoa proteins, and (iii) adjusting the pH level of the precipitated cocoa proteins, and performing membrane filtration and spray drying of the precipitated cocoa proteins, to obtain cocoa proteins;

j) treating the cocoa composition produced in step (g) with proteases enzymes via ultrasonication followed by spray drying to obtain cocoa protein hydrolysates; and k) (i) preparing a water solution of the free flowing procyanidin type B polymer-rich polyphenolic extract obtained in step (c) and a water solution of the soluble fiber obtained in step (h), (ii) mixing the water solutions of step k) (i) together in the presence or absence of other soluble fibers under homogenization conditions, and (iii) spray drying the mixture of the water solutions to produce a composition of cocoa fiber encapsulated cocoa polyphenols.

2. The method according to claim 1, wherein the cocoa beans are fermented or unfermented.

3. The method according to claim 1, wherein the cutting, flaking and powdering of the dried cocoa beans performed in step a) (i) results in cocoa bean particles having a mesh size in a range from approximately 1.0 mm to approximately 10 mm.

4. The method according to claim 1, wherein the evaporation in step a) (iii) is carried out at a temperature in a range from approximately 40° C. to approximately 60° C.

5. The method according to claim 1, wherein the pressure in step a (iii) is in a range from approximately 600 mmHg to approximately 750 mmHg.

6. The method according to claim 1, wherein the supernatant solution in step h) (iii) has a pH in a range from approximately 2 to approximately 5.

7. The method according to claim 1, wherein the emulsifier of step b (ii) comprises sugar syrup, glycerol, propylene glycol or the like.

8. The method according to claim 1, wherein the pH of the alkaline solution of step i) (i) is a in the range from approximately 10 to approximately 12.

9. The method according to claim 1, wherein the mineral acid in step i) (ii) is selected from the group consisting of: hydrochloric acid, sulphuric acid, and phosphoric acid.

10. The process method to claim 1, wherein the protease enzyme of step (j) is selected from animal origin, vegetable origin or microbial origin.

11. The method according to claim 1, wherein the solvent extraction of step (a) is carried out directly on cocoa beans that have not undergone defatting process.

12. The method according to claim 1, wherein the polyphenol content of the extract of step (c) is in a range from approximately 950 mg per 1000 mg to approximately 990 mg per 1000 mg gallic acid equivalent, and wherein the extract obtained in step f) (iii) includes procyanidin oligomers in a range from approximately 400 mg per 1000 mg to approximately 700 mg per 1000 mg.

13. The method according to claim 1, wherein total polyphenol of the extract of step (c) is in a range from approximately 700 mg per 1000 mg to approximately 800 mg per 1000 mg gallic acid equivalent, and wherein the extract obtained in step f) (iii) includes procyanidin oligomers in a range from approximately 300 mg per 1000 mg to approximately 500 mg per 1000 mg.

14. The method according to claim 1, wherein the cocoa residue obtained in step a) (i) is dried under vacuum at a temperature in a range from approximately 50 to approximately 70° C. and powdered to produce composition of tasteless cocoa dietary fiber with a mild characteristic smell of chocolate, containing not less than 55% total dietary fiber, not less than 25% proteins, and not less than 15% carbohydrates.

15. The method according to claim 1, wherein the solvent extract obtained in step a) (i) is roasted with sugar syrup at a temperature in a range from approximately 100° C. to approximately 120° C. for a duration of time in a range from approximately 4 hours to approximately 6 hours to produce a chocolate flavored solvent extract, the chocolate flavored solvent extract having a composition of cocoa fat of about 10% to about 20%, carbohydrates of about 35% to about 50%, proteins of about 15% to about 25% and theobromine of about 3% to about 6%.

16. The method of claim 1, wherein the aqueous admixture of polar organic solvents in step a) (i) is a solution having contents selected from the group consisting of: water alone, a mixture of water and acetone, or a mixture of water and alcohol.

* * * * *